(12) United States Patent
Bevilacqua et al.

(10) Patent No.: US 11,298,401 B2
(45) Date of Patent: *Apr. 12, 2022

(54) COMPOSITIONS AND USES OF ANTIMICROBIAL MATERIALS WITH TISSUE-COMPATIBLE PROPERTIES

(71) Applicant: AMICROBE, INC., Carlsbad, CA (US)

(72) Inventors: Michael P. Bevilacqua, Boulder, CO (US); Diego Benitez, Santa Monica, CA (US); Jarrod A. Hanson, Covina, CA (US)

(73) Assignee: Amicrobe, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/240,197

(22) Filed: Aug. 18, 2016

(65) Prior Publication Data

US 2017/0042965 A1 Feb. 16, 2017

Related U.S. Application Data

(63) Continuation of application No. 14/385,752, filed as application No. PCT/US2013/032535 on Mar. 15, 2013, now Pat. No. 9,446,090.

(60) Provisional application No. 61/615,150, filed on Mar. 23, 2012, provisional application No. 61/625,757, filed on Apr. 18, 2012, provisional application No. 61/625,760, filed on Apr. 18, 2012, provisional application No. 61/716,242, filed on Oct. 19, 2012.

(51) Int. Cl.
| | |
|---|---|
| *A61K 38/16* | (2006.01) |
| *A01N 37/46* | (2006.01) |
| *A01N 37/44* | (2006.01) |
| *A61L 15/42* | (2006.01) |
| *A61L 15/46* | (2006.01) |
| *A61L 24/00* | (2006.01) |
| *A61K 9/06* | (2006.01) |
| *A61K 31/715* | (2006.01) |
| *A61K 31/765* | (2006.01) |
| *A61K 38/02* | (2006.01) |
| *A61K 45/06* | (2006.01) |
| *A01N 47/44* | (2006.01) |

(52) U.S. Cl.
CPC ............ *A61K 38/16* (2013.01); *A01N 37/44* (2013.01); *A01N 37/46* (2013.01); *A01N 47/44* (2013.01); *A61K 9/06* (2013.01); *A61K 31/715* (2013.01); *A61K 31/765* (2013.01); *A61K 38/02* (2013.01); *A61K 45/06* (2013.01); *A61L 15/42* (2013.01); *A61L 15/46* (2013.01); *A61L 24/001* (2013.01); *A61L 24/0015* (2013.01); *A61L 24/0036* (2013.01); *A61L 2400/04* (2013.01); *Y02A 50/30* (2018.01)

(58) Field of Classification Search
None
See application file for complete search history.

(56) References Cited

U.S. PATENT DOCUMENTS

| | | |
|---|---|---|
| 6,632,922 B1 | 10/2003 | Deming et al. |
| 6,680,365 B1 | 1/2004 | Deming |
| 6,686,446 B2 | 2/2004 | Deming et al. |
| 6,818,732 B2 | 11/2004 | Deming et al. |
| 7,279,458 B2 | 10/2007 | Fatheree et al. |
| 7,329,727 B2 | 2/2008 | Deming |
| 7,847,059 B2 | 12/2010 | O'Neil |
| 8,088,888 B2 | 1/2012 | O'Neil |
| 8,138,144 B2 | 3/2012 | Krieger et al. |
| 8,350,003 B2 | 1/2013 | O'Neil |
| 8,470,769 B2 | 6/2013 | O'Neil |
| 9,017,730 B2 * | 4/2015 | Bevilacqua ............ A23L 3/3526 424/491 |
| 9,446,090 B2 * | 9/2016 | Bevilacqua ............ A61K 38/16 |
| 2007/0190110 A1 | 8/2007 | Pamerijer et al. |
| 2008/0125581 A1 | 5/2008 | Deming et al. |
| 2010/0003336 A1 | 1/2010 | Deming et al. |
| 2013/0267458 A1 * | 10/2013 | Bevilacqua ............ A23L 3/3526 514/2.7 |
| 2015/0080290 A1 | 3/2015 | Bevilacqua et al. |
| 2015/0225458 A1 | 8/2015 | Rapsch et al. |
| 2016/0120936 A1 | 5/2016 | Troxel |
| 2021/0100867 A1 | 4/2021 | Bevilacqua et al. |

FOREIGN PATENT DOCUMENTS

| | | |
|---|---|---|
| CN | 102171238 A | 8/2011 |
| CN | 101031583 B | 6/2013 |
| CN | 110740744 A | 1/2020 |
| EP | 1002547 A1 | 5/2000 |
| EP | 1 473 584 A1 | 11/2004 |
| EP | 2096118 A1 | 9/2009 |
| EP | 1778720 B1 | 9/2010 |

(Continued)

OTHER PUBLICATIONS

Anonymous, Save-ory TM GL610 General Information, Internet Citation, Feb. 9, 2006, XP002366870, Retrieved from the internet: URL:http://www.save-ory.com/documents/gigl610.pdf.

(Continued)

*Primary Examiner* — Christina Bradley

(74) *Attorney, Agent, or Firm* — Knobbe, Martens, Olson & Bear, LLP

(57) ABSTRACT

Compositions comprising a mixture of an antimicrobial cationic polypeptide and a second pharmaceutically-acceptable polymer are disclosed, as well as methods and uses thereof for the treatment and prevention of infections that occur when our natural barriers of defense are broken.

17 Claims, 30 Drawing Sheets

Specification includes a Sequence Listing.

(56) References Cited

FOREIGN PATENT DOCUMENTS

| | | | |
|---|---|---|---|
| EP | 2272897 A1 | 1/2011 | |
| EP | 2359859 A1 | 3/2011 | |
| EP | 2292270 A1 | 8/2011 | |
| EP | 2 666 484 A1 | 11/2013 | |
| EP | 2827841 | 1/2015 | |
| EP | 1927597 B1 | 11/2016 | |
| EP | 3141559 A1 | 3/2017 | |
| EP | 3147293 A1 | 3/2017 | |
| EP | 3606543 A1 | 2/2020 | |
| JP | 2003-171463 A | 6/2003 | |
| JP | 2005-504769 | 2/2005 | |
| JP | 2007-517027 | 6/2007 | |
| JP | 2010-527335 | 8/2010 | |
| JP | 2010-531189 | 9/2010 | |
| JP | 2010-537997 | 12/2010 | |
| JP | 2016-113373 A | 6/2016 | |
| JP | 6224069 B2 | 11/2017 | |
| KR | 1020100049039 | 5/2010 | |
| KR | 1020110095867 | 8/2011 | |
| KR | 1020120003893 | 1/2012 | |
| RU | 2180855 C2 | 3/2002 | |
| RU | 2415150 C2 | 3/2011 | |
| WO | WO 1994/020041 A1 | 9/1994 | |
| WO | WO 2000/050006 | 8/2000 | |
| WO | WO 2002/026209 | 4/2002 | |
| WO | WO 2003/015809 | 2/2003 | |
| WO | WO 2005/018701 A1 | 3/2005 | |
| WO | WO 2005/094891 A2 | 10/2005 | |
| WO | WO 2006/018652 A3 | 2/2006 | |
| WO | WO 2009/001087 | 12/2008 | |
| WO | WO 2009/032605 A2 | 3/2009 | |
| WO | WO 2010/038040 A1 | 4/2010 | |
| WO | WO 2010/083589 A1 | 7/2010 | |
| WO | WO-2011134998 A1 * | 11/2011 | ............... C12N 9/52 |
| WO | WO 2012/027411 A2 | 3/2012 | |
| WO | WO-2012027411 A2 * | 3/2012 | ........... A23L 3/3526 |
| WO | WO 2012/098653 A1 | 7/2012 | |
| WO | WO 2012/135685 A1 | 10/2012 | |
| WO | WO 2013/142374 | 9/2013 | |
| WO | WO 2016/044683 A1 | 3/2016 | |
| WO | WO 2018/187617 A1 | 10/2018 | |
| WO | WO 2019/169324 A1 | 9/2019 | |

OTHER PUBLICATIONS

International Preliminary Report on Patentability, PCT Application No. PCT/US2013/032535, dated Mar. 23, 2012, in 7 pages.

International Search Report and Written Opinion dated May 9, 2013, PCT/US2013/032535.

Sperling, L.H., Introduction to Physical Polymer Science, 1986, pp. 111-116, John Wiley & Sons, U.S.

Vidaza (azacitidine for injection) Product Label, Approved 2004; Revised: Aug. 2011, Reference ID: 3002164.

Bjarnsholt, T., "The Role of Bacterial Biofilms in Chronic Infections," Acta Pathologica, Microbiologica et. Immunologica Scandinavica (2013) 121 (Suppl. 136): 1-51.

Dobry A. et al., "Phase Separation in Polymer Solution," Journal of Polymer Science, vol. 2, No. 1, pp. 90-100, 1947.

Katchalski, E. et al. "The Action of Some Water-soluble Poly-α-amino Acids on Bacteria" Biochemical Journal (1953) vol. 55, pp. 671 to 680.

Davies, D. "Understanding Biofilm Resistance to Antibacterial Agents." Nature Reviews—Drug Discovery, vol. 2, Feb. 2003, pp. 114-122.

Isaksson, K. et al. "In vivo toxicity and biodistribution of intraperitoneal and intravenous poly-L-lysine and poly-L-lysine/poly-L-glutamate in rats", Journal of Materials Science: Materials in Medicine (2014) vol. 25, pp. 1293 to 1299.

Bevilacqua, M. et al. "Amino Acid Block Copolymers with Broad Antimicrobial Activity and Barrier Properties," Macromolecular Bioscience vol. 17, No. 10, Mar. 1, 2017, in 9 pages, ISSN: 1616-5187, DOI: 10.1002/mabi.201600492.

* cited by examiner

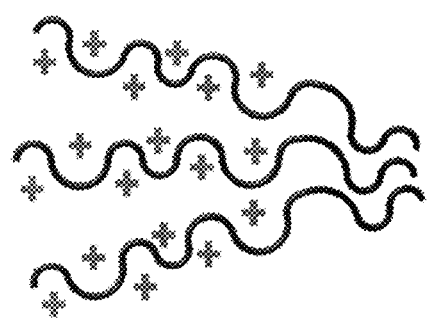
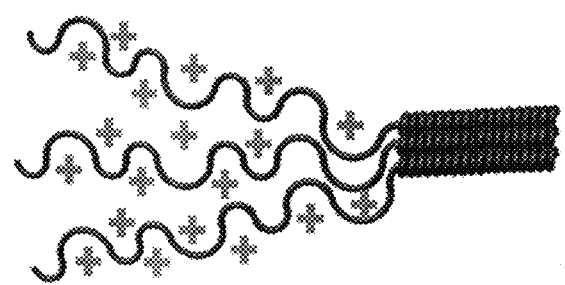
FIG. 1A
FIG. 1B

FIG. 2A

| | | | |
|---|---|---|---|
| [K$_{65}$(rac-L)$_{15}$-RAN]-(rac-L)$_{20}$ | K$_{100}$(rac-L)$_{20}$ | K$_{120}$(rac-L)$_{10}$ | K$_{130}$-L$_{40}$-RAN |
| K$_{80}$(rac-L)$_{20}$ | K$_{100}$L$_{40}$ | K$_{130}$L$_{20}$ | K$_{130}$L$_{60}$ |
| K$_{100}$ | K$_{100}$(rac-L)$_{40}$ | K$_{130}$(rac-L)$_{20}$ | K$_{130}$(rac-L)$_{60}$ |
| K$_{100}$-L$_{20}$ | K$_{100}$-L$_{40}$-RAN | K$_{130}$-L$_{30}$ | K$_{150}$-L$_{30}$ |
| K$_{100}$(rac-L)$_{20}$ | K$_{100}$-L$_{50}$ | K$_{130}$(rac-L)$_{30}$ | K$_{160}$(rac-L)$_{20}$ |
| K$_{100}$(rac-L)$_{20}$-RAN | K$_{100}$-L$_{60}$ | K$_{130}$-L$_{40}$ | K$_{180}$(rac-L)$_{20}$ |
| K$_{100}$-L$_{30}$ | K$_{100}$(rac-L)$_{60}$ | K$_{130}$(rac-L)$_{40}$ | K$_{200}$-L$_{50}$ |

FIG. 2B

| | | | |
|---|---|---|---|
| K$_{55}$ | K$_{180}$L$_{54}$ | K$_{360}$L$_{72}$ | E$_{324}$L$_{36}$ |
| K$_{99}$L$_{36}$ | K$_{180}$(rac-L)$_{54}$ | K$_{360}$(rac-L)$_{72}$ | E$_{360}$L$_{36}$ |
| K$_{99}$(rac-L)$_{36}$ | K$_{324}$L$_{36}$ | E$_{180}$ | E$_{360}$(rac-L)$_{36}$ |
| K$_{99}$(rac-L)$_{36}$-RAN | K$_{360}$ | E$_{180}$-L$_{18}$ | E$_{360}$L$_{54}$ |
| K$_{180}$ | K$_{360}$L$_{36}$ | E$_{180}$(rac-L)$_{18}$ | E$_{360}$(rac-L)$_{54}$ |
| K$_{180}$-L$_{18}$ | K$_{360}$(rac-L)$_{36}$ | E$_{180}$(rac-L)$_{36}$ | E$_{360}$L$_{72}$ |
| K$_{180}$(rac-L)$_{18}$ | K$_{360}$L$_{36}$-RAN | E$_{180}$L$_{54}$ | E$_{360}$(rac-L)$_{72}$ |
| K$_{180}$L$_{36}$ | K$_{360}$L$_{54}$ | E$_{180}$(rac-L)$_{54}$ | |
| K$_{180}$(rac-L)$_{36}$ | | | |

|  | 10 ug/mL | | 100 ug/mL | |
| --- | --- | --- | --- | --- |
|  | 5 min | 60 min | 5 min | 60 min |
| S. aureus | 4 | ≥6 | ≥6 | 5 |
| P. aeruginosa | 5 | ≥6 | ≥6 | ≥6 |

FIG. 11A

|  | 10 ug/mL* | | 100 ug/mL** | |
| --- | --- | --- | --- | --- |
|  | 5 min | 60 min | 5 min | 60 min |
| S. aureus | 4 | ≥6 | ≥6 | ≥6 |
| P. aeruginosa | 4 | ≥6 | ≥6 | ≥6 |

\* With 10 ug/mL poloxamer407
\*\* With 100 ug/mL poloxamer407

FIG. 11B

| $K_{100}(rac\text{-}L)_{20}$ | | Log Reduction - 60 min | |
|---|---|---|---|
| | | 10 µg/mL | 100 µg/mL |
| Gram-positive bacteria | Staphylococcus aureus (MRSA) | 5 | 5 |
| | Staphylococcus epidermidis | ≥6 | 5 |
| | Enterococcus faecium (VRE) | 5 | ≥6 |
| Gram-negative bacteria | Acinetobacter baumannii | ≥6 | ≥6 |
| | Bacteroides fragilis | 2 | ≥6 |
| | Enterobacter cloacae | 5 | ≥6 |
| | Escherichia coli | ≥6 | ≥6 |
| | Klebsiella pneumoniae | ≥6 | 5 |
| | Proteus mirabilis | ≥6 | ≥6 |
| | Serratia marcescens | ≥6 | ≥6 |
| Fungi | Candida albicans | ≥5 | ≥5 |

FIG. 12

|  |  | S. aureus | S. epidermidis | P. aeruginosa | E. coli |
|---|---|---|---|---|---|
| 10 µg/mL K100L40 | -- | 1 | 6 | ≥6 | 5 |
|  | 20 µg/mL HEC | 2 | ≥7 | 5 | 5 |
|  | 200 µg/mL HEC | 3 | ≥6 | 4 | 5 |
| 100 µg/mL K100L40 | -- | 1 | 6 | ≥6 | ≥6 |
|  | 200 µg/mL HEC | 3 | ≥7 | ≥6 | ≥6 |
|  | 2000 µg/mL HEC | 3 | ≥7 | 5 | ≥6 |

*FIG. 16*

| Polymer | Firmness[a] (+/- s.d.) (mN) | Firmness (+/- s.d.) w/ HEC[b] (mN) | Firmness Interaction Parameter (mN)[c] | Work of Adhesion[a] (+/- s.d.) (mN•mm) | Work of Adhesion w/HEC[b] (+/- s.d.) (mN•mm) | Work of Adhesion Interaction Parameter (mN•mm)[c] |
|---|---|---|---|---|---|---|
| $K_{100}$ | 2.34 (0.20) | 4.34 (0.07) | -3.38 | 6.92 (0.41) | 16.21 (0.30) | -14.61 |
| $K_{200}$ | 2.17 (0.07) | 5.49 (0.16) | -2.06 | 6.21 (1.17) | 18.92 (0.21) | -11.20 |
| $K_{100}(rac\text{-}L)_{20}$ | 2.18 (0.11) | 4.76 (0.25) | -2.80 | 6.99 (0.08) | 17.93 (0.56) | -12.96 |
| $K_{100}(rac\text{-}L)_{40}$ | 2.51 (0.13) | 12.47 (0.34) | 4.58 | 8.64 (0.18) | 40.19 (0.63) | 7.64 |
| $K_{100}L_{20}$ | 2.37 (0.14) | 8.29 (0.19) | 0.55 | 6.80 (0.70) | 23.64 (0.48) | -7.07 |
| $K_{100}L_{40}$ | 2.94 (0.25) | 22.77 (0.90) | 14.45 | 22.60 (0.59) | 79.43 (2.33) | 32.93 |
| HEC | 5.38 (0.32) | - | - | 23.90 (0.62) | - | - |

FIG. 21

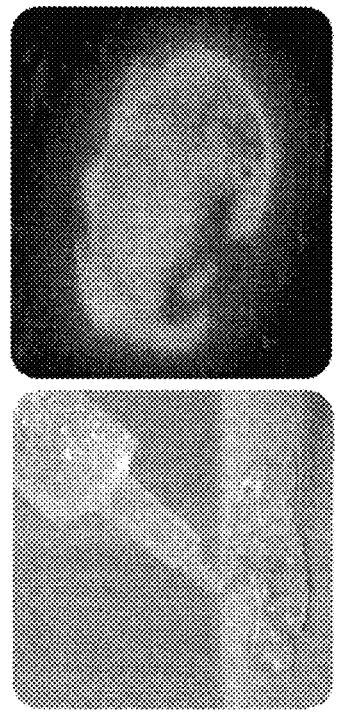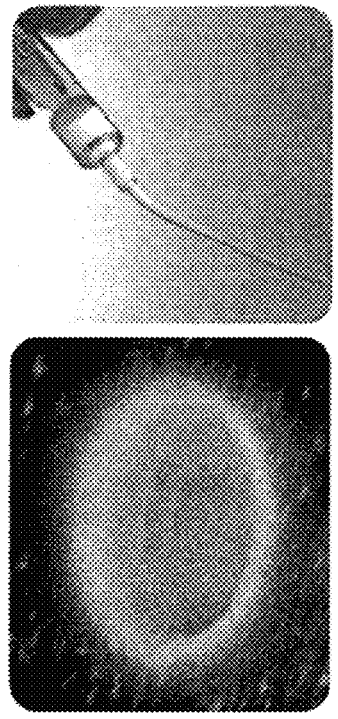
FIG. 23

COMPOSITIONS AND USES OF ANTIMICROBIAL MATERIALS WITH TISSUE-COMPATIBLE PROPERTIES

INCORPORATION BY REFERENCE TO ANY PRIORITY APPLICATIONS

This application is a continuation of U.S. patent application Ser. No. 14/385,752, filed on Sep. 16, 2014, which is the U.S. National Phase entry of International Application PCT/US2013/032535, filed on Mar. 15, 2013, which claims the benefit of priority to U.S. Provisional Application No. 61/615,150, filed on Mar. 23, 2012, U.S. Provisional Application No. 61/625,757, filed on Apr. 18, 2012, U.S. Provisional Application No. 61/625,760, filed on Apr. 18, 2012, and U.S. Provisional Application No. 61/716,242, filed on Oct. 19, 2012, the disclosures of each of which are hereby incorporated by reference in their entireties for all purposes.

REFERENCE TO SEQUENCE LISTING

The present application is being filed along with a Sequence Listing in electronic format. The Sequence Listing is provided as a file entitled AMIC001C1SeqListing.TXT, which was created and last modified on Sep. 15, 2020 and is 44,633 bytes in size. The information in the electronic Sequence Listing is hereby incorporated by reference in its entirety.

BACKGROUND OF THE INVENTION

When barriers are broken, infections occur. Surgery, trauma and burns, medical instrumentation (e.g., catheterization, ventilation), chronic wounds (e.g., diabetic foot ulcers) and a variety of diseases disrupt our natural barriers of defense. In nearly all cases, these "wounds" become contaminated with microbes. Then, the terrain of wounds provides an excellent environment for microbial growth. The battle begins, and it's trench warfare. Damaged tissues ('cracks and crevices'), altered blood flow and exudate production, changes in local temperature, pH and tissue oxygenation, as well as the lack of commensal bacteria, can all contribute. Also, bleeding and vascular leakage may provide fluids and nutrients that ultimately support microbial growth. Bacterial or fungal colonization, and/or overt infection may occur. Microbial biofilms can help microbes to create their own local environments. Various surgical, trauma and medical settings all involve disruption of our natural barriers of defense and deserve special attention because the outcomes can range from rapid cure to lethal sepsis.

Natural barriers are typically referred to by their anatomical sites such as skin, pulmonary epithelium, gastrointestinal mucosa, etc. These names may imply a level of simplicity that is unwarranted. These barriers are often both passive and active. They can involve a variety of cells, secreted glycoproteins, matrix components and fluids that act in concert to provide effective defense against microbial invasion. In some sites, resident microbes contribute to the barrier action against other potential invaders. Under most circumstances, these physical and functional barriers are highly effective. However, they can be broken rather easily by mechanical or chemical insults. In addition, certain systemic diseases can weaken our natural barriers and increase the risk of breakdown, as occurs in diabetic foot ulcers or cystic fibrosis. Finally, a first infection can weaken host defenses against a second infection, as occurs in influenza followed by bacterial pneumonia or *Trichomonas vaginalis* followed by certain sexually transmitted diseases (e.g., HIV).

Broken barriers of defense leave the host susceptible to infection by a wide variety of microbes, ranging from typically benign commensal organisms to aggressive pathogens. Commonly, we are our own source of the microbes that contaminate our wounds. The human body hosts a very large number of bacteria, predominately on skin, in mouths and within lower GI tracts. It has been estimated that there are more bacterial cells ($10^{14}$) than mammalian cells ($10^{13}$) within the space of one human body. Despite this close relationship with microbes, most of our tissues (including blood, subcutaneous tissue, muscle, brain) remain sterile until the disruption of the natural barriers. Other people and environmental sources of microbes are also important, especially in healthcare settings. Once a barrier is broken, microbial contamination, critical level colonization, biofilm formation and/or overt infection may occur. Polymicrobial colonization and/or infection is common in certain settings (e.g., diabetic foot ulcers, complex intra-abdominal infections), and may involve aerobes, anaerobes or both.

Prior approaches to the prevention and treatment of these infections have demonstrated substantial weaknesses. Both lack of effectiveness and tissue toxicity have been challenges. Antimicrobials often fail to get to the right tissue spaces and/or fail to remain active for sufficient time to prevent or treat infection. Complex surfaces like those of the abdominal cavity or large burns are particularly difficult to cover effectively. Finally, safe application of sufficient antimicrobial materials into certain tissue spaces (such as through laparoscopic or arthroscopic equipment) can be challenging. Antimicrobials that are readily applied by these methods tend to be solution-based materials with limited ability to bind tissues and remain active over time.

Biofilms present a particular challenge. Increasing evidence points to the resistance of bacterial biofilms to a variety of antimicrobial approaches and to their role in adverse patient outcomes. These microbial communities resist traditional antiseptics and antibiotics through several mechanisms, including, but not limited to, their own production of extracellular polymeric substances, which are often negatively charged (anionic). Penetration of these materials by traditional antimicrobials is often limited. For example, in acute wounds (e.g. surgery and trauma), devitalized tissue and foreign bodies (e.g., prosthetic implants) may support biofilm formation and thereby increase the probability of overt infection. In chronic wounds (e.g. diabetic foot ulcers), biofilms may persist and lead to delayed wound healing. Medical instruments like ventilators and catheters can be a site of biofilm formation and provide a source of infection.

Antimicrobial treatment of early infections may alter the course of the infection, resulting in more resistant and more dangerous infections. Common antimicrobial strategies focus on the use of selective antibiotics (e.g., penicillin for gram-positive organisms) in order to avoid the development of bacteria that are resistant to broad-spectrum antibiotics. Inadvertently, this important strategy can have negative outcomes on an individual patient, where targeted antibiotics result in the emergence of an aggressive, different microorganism (e.g., *Pseudomonas*). In this way, treated wounds can become the site for a "parade of pathogens", where an early, dominant microbial species (e.g., Staph *aureus*) is replaced by a second (e.g., MRSA, methicillinresistant Staph *aureus*) and, perhaps, even a third and fourth microbial species (e.g., a multi-drug resistant gram negative species).

The large numbers of adverse patient outcomes in today's advanced healthcare settings underscore the inadequacies of prior art in the prevention and treatment of these infections. Several key weaknesses include:

1. Low antimicrobial activity in tissue settings and on biofilms;
2. Inadequate distribution to the relevant tissue space;
3. Limited, if any, barrier activity;
4. Narrow breadth of antimicrobial activity enables the "parade of pathogens";
5. Inadequate treatment fosters more antimicrobial resistance; and/or
6. Tissue toxicity.

Infections of wounds and other broken-barrier settings are common and costly. In the US alone, approximately 12 million traumatic injuries are treated in emergency departments each year. In addition, there are more than 50 million surgeries (inpatient and outpatient). The US Department of Health and Human Services indicates that there are more than 1.7 million healthcare-associated infections annually, resulting in approximately 100,000 deaths and $30 billion in healthcare costs per year. Many of these healthcare-associated infections start with broken barriers. Examples include surgical site infections (SSIs), catheter-associated urinary tract infections and ventilator-associated pneumonia. The chronic wounds associated with pressure ulcers (bed sores) and diabetic foot ulcers present their own unique challenges.

In addition to infection, several other wound-associated outcomes remain major challenges. These include blood loss, tissue adhesions/scarring, and poor wound healing. And, in some cases, known antimicrobial treatments make these problems worse. Certain antimicrobial wound treatments (including antibiotic washes) can result in excessive tissue responses (e.g., tissue adhesions or scarring). Certain antiseptic/antimicrobial materials may alter wound healing, resulting in insufficient tissue responses (e.g., poor wound healing, poor wound strength).

Effective hemostasis in wounds also remains a substantial problem. Hemostatic materials have been described and are utilized in a variety of settings, including in trauma and in surgery. While effective in some situations, these materials do not provide ideal solutions to the challenges. First, there are times when the hemostasis is insufficient and too much bleeding occurs, potentially with lethal consequences. In some of these cases initial hemostasis occurs, however, subsequent re-bleeding occurs. This may be due to fibrinolytic activity. In addition to the problems resulting from blood loss, extravasated blood components in the tissues may contribute to additional adverse outcomes including infection and the fibrotic responses seen with post-surgical tissue adhesions. Second, in some cases, hemostatic materials cause problems by entering the blood stream and causing clotting (thrombosis) within blood vessels, potentially with lethal outcomes. Third, in some cases, wound treatment materials (including hemostatic materials) can serve as a site for subsequent infection or can result in abnormal tissue responses such as adhesion formation and/or tissue scarring, resulting in adverse medical outcomes. Improved approaches to hemostasis are needed.

SUMMARY OF THE INVENTION

In accordance with embodiments of the invention, a mixture of an antimicrobial cationic polypeptide and a second pharmaceutically-acceptable polymer is used in the treatment and prevention of infections that occur when our natural barriers of defense are broken. These novel compositions can provide two functions: direct antimicrobial activity and barrier activity. Embodiments of the invention addresses one or more weaknesses of previous antimicrobials described above. Notably, it has been recognized that the effectiveness of most of the previous antiseptics and antibiotics were based on determinations of antimicrobial activity in solution with the microbes in suspension (MIC assays), producing results that are not necessarily indicative of effectiveness in tissues, and thus could lead away from determining effectiveness in tissues. By contrast, the inventors focused on the design and selection of agents for broad antimicrobial activity, especially at tissue surfaces and in the terrain ("cracks and crevices") of wounds. This includes the formation of a barrier containing cationic (positively charged) elements that can inhibit the movement of certain substances or cells that display anionic elements (e.g., microbes). In one embodiment, the synthetic cationic polypeptides of these compositions contain at least one cationic segment and at least one hydrophobic segment, are comprised substantially of natural amino acids, and are broadly antimicrobial (i.e., against gram positive and gram negative bacteria). They can also be designed to self-assemble, based in part on the interaction of their hydrophobic segments. Further, synthetic polypeptides are formulated with a second pharmaceutically-acceptable polymer to provide a composition that is directly antimicrobial and that effectively coats tissues. These mixtures may also display hemostatic properties. In some embodiments, the second pharmaceutically acceptable polymer is not a polyethylene glycol (PEG).

Embodiments of the invention may be used alone or in combination with other materials that provide similar or complementary activities.

An embodiment provides aqueous composition for the prevention, inhibition, or treatment of infection comprising: a mixture comprising one or more synthetic, cationic polypeptide(s) with antimicrobial activity; and a second pharmaceutically-acceptable polymer that is not a synthetic, cationic polypeptide(s) with antimicrobial activity; wherein the amounts of the one or more synthetic, cationic polypeptide(s) and the second pharmaceutically-acceptable polymer are each at least about 100 μg/mL based on the total volume of the aqueous composition; wherein the amount of the second pharmaceutically-acceptable polymer is at least about 10% by weight, based on the weight of the one or more synthetic, cationic polypeptide(s); and wherein the synthetic, cationic polypeptide(s) and the second pharmaceutically-acceptable polymer are mutually miscible in water.

The synthetic, cationic polypeptide(s) with antimicrobial activity and the second pharmaceutically-acceptable polymer are considered mutually miscible if at least about 90% of the polymeric components remain mutually soluble 24 hours after mixing and maintaining at room temperature in water at a concentration of each polymer of 1 mg/mL, upon visible examination.

In another embodiment, one or more of the synthetic cationic polypeptide(s) in the aqueous composition comprises a segment having a chain length of at least 40 amino acid residues.

In another embodiment, the synthetic cationic polypeptide(s) in the aqueous composition comprises substantially all natural amino acid subunits.

In another embodiment, the synthetic cationic polypeptide(s) in the aqueous composition is characterized by at least one segment containing at least five consecutive cationic amino acid residues and at least one segment containing at least five consecutive hydrophobic amino acid residues.

In another embodiment, the second pharmaceutically-acceptable polymer in the aqueous composition is selected from the group consisting of cellulose, alginate, collagen, polymeric surfactant, polyethylene glycol, polyvinyl alcohol, polyurethane, polyvinyl pyrolidinone (PVP), fibrin(ogen), blood proteins and tissue proteins.

In another embodiment, the antimicrobial activity of the aqueous composition is greater than 3 logs killing of *Staphylococcus epidermidis* and *Escherichia coli* in standard 60 minute time-kill assays at a synthetic cationic polypeptide(s) concentration of 100 µg/mL or less.

In another embodiment, the aqueous composition is further characterized by the ability to disrupt or inhibit a biofilm in vitro at a total polymer concentration of 40 mg/ml or less.

In another embodiment, the aqueous composition is further characterized by a barrier activity, as measured by a decrease in the diffusion rate of an anionic dye of more than 2 logs at a total polymer concentration of 40 mg/mL or less.

In another embodiment, the aqueous composition is further characterized by a storage modulus of at least 50 Pa at a total polymer concentration of less than 40 mg/mL.

In another embodiment, the aqueous composition is further characterized by a storage modulus of at least 50 Pa at a total polymer concentration of less than 40 mg/mL and an ability to pass through a 20 g needle using less than 60 N pressure.

In another embodiment, the aqueous composition is further characterized by an ability to pass through a 20 g needle and recover a minimum of 70% of its strength as measured by storage modulus within 10 minutes.

In another embodiment, the aqueous composition is in the form of a solution, a gel, a cream, a foam, or a dressing.

In another embodiment, the aqueous composition is further characterized as being in combination with, or binding to, a dressing material, including but not limited to a gauze or sponge.

In another embodiment, the aqueous composition has pro-coagulant activity, pro-hemostatic activity, or both.

In another embodiment, the aqueous composition further comprises an active pharmaceutical ingredient (API) selected from the group consisting of steroid, pro-inflammatory agent, anti-inflammatory agent, anti-acne agent, preservatives hemostatic agent, angiogenic agent, wound healing agent, anti-cancer agent and other antimicrobial agent.

Another embodiment provides a use of any one of the aqueous compositions described herein for any one or more selected from the group consisting of prevention of infections, treatment of infections, treatment for topical anti-infection, treatment for microbial decolonization, wound treatment, surgical site treatment, trauma treatment, burn treatment, treatment of diabetic foot ulcers, eye treatment, treatment of vaginal infections, treatment of urinary tract infections, hand sanitization, for coating prosthetic devices and/or implants, food preservation and solution preservation.

Another embodiment provides a method for the prevention and/or treatment of infections comprising: contacting a tissue of a patient subject with any of the aqueous compositions described herein.

In another embodiment, the method further comprises applying negative-pressure to a wound.

In another embodiment, the method further comprises treating the patient systemically with other antibiotics and/or locally with another antimicrobial, and/or at least one selected from the group consisting of an antibiotic, an anti-biofilm agent, a surfactant, and a combination thereof.

BRIEF DESCRIPTION OF THE DRAWINGS

FIGS. 1A and 1B depict examples of synthetic cationic polypeptides, $K_x(\text{rac-L})_y$ and $K_xL_y$, respectively. These polypeptides contain a cationic segment of lysine amino acids and a hydrophobic segment of leucine amino acids. The cationic segments provide for multimeric interaction with anionic substances, including bacterial surfaces. The hydrophobic segments associate in aqueous media, leading to the formation of various structures, such as multimers in solution, micelles, sheets, and fibrils. These hydrophobic interactions are important in barrier formation.

FIGS. 2A and 2B are tables that show examples of synthetic cationic polypeptides synthesized using either (A) an amine (shown in FIG. 2A) or (B) an organometallic $Co(PMe_3)_4$ initiator (shown in FIG. 2B).

FIGS. 11A and 11B show in vitro antimicrobial time-kills of $K_{100}(\text{rac-L})_{20}$ (SEQ ID NO: 12) and 1:1 $K_{100}(\text{rac-L})_{20}$ (SEQ ID NO: 12):Poloxamer 407 solutions, respectively, at concentrations of 10 and 100 µg/mL against *S. aureus* (29213), and *P. aeruginosa* (27853) after 5 and 60 min.

FIG. 12 is a table (Table 3) that shows an in vitro antimicrobial time-kill of $K_{100}(\text{rac-L})_{20}$ (SEQ ID NO: 12) solutions at concentrations of 10 and 100 µg/mL against a variety of gram positive and gram negative bacteria and fungi after 60 min contact time.

FIG. 16 is a table (Table 4) that shows an in vitro antimicrobial time kill assay against *S. aureus* (29213), *S. epidermidis* (RMA 18291), *P. aeruginosa* (27853), and *E. coli* (25922) after 60 min. contact time. $K_{100}L_{40}$ (SEQ ID NO: 19) at concentrations of 10 and 100 µg/mL with other ratios of hydroxyethyl cellulose: 1:2 $K_{100}$(rac-L)$_{20}$ (SEQ ID NO: 12):HEC and 1:20 $K_{100}$(rac-L)$_{20}$ (SEQ ID NO: 12) were tested.

FIG. 17A shows that a 2% synthetic cationic polypeptide preparation ($K_{100}L_{40}$ (SEQ ID NO: 19)) was highly effective in blocking the diffusion of a colored, anionic dye over a 48 hour period. By contrast, as shown in FIG. 17B, the dye diffused readily (within 5 minutes) through a 2% PEG (10,000) preparation.

FIG. 21 is a table (Table 5) that shows synthetic cationic polypeptide texture analysis profile data of pure polypeptides and HEC mixtures. a. Values for 1% (w/w) polypeptide in water. b. Values for 1% polypeptide/1% HEC (w/w) in water. c. Interaction parameter: $\Delta F = F_{mix(poly/HEC)} - (F_{poly} + F_{HEC})$. Where $F_{mix(poly/HEC)}$=firmness of 1% polypeptide/1% HEC, $F_{poly}$=firmness of 1% polypeptide solution, and $F_{HEC}$=firmness of 1% HEC (Natrosol HHX) in water. Similar treatment of data was performed for the work of adhesion interaction parameter.

FIG. 23 demonstrates that synthetic cationic polypeptide solutions (anti-infective solutions; left) and synthetic cationic polypeptide hydrogels (barrier gel; right) are effective at coating open wounds in a porcine model. Synthetic cationic polypeptides were fluorescently-labeled.

DETAILED DESCRIPTION OF THE PREFERRED EMBODIMENT

Figure 3:
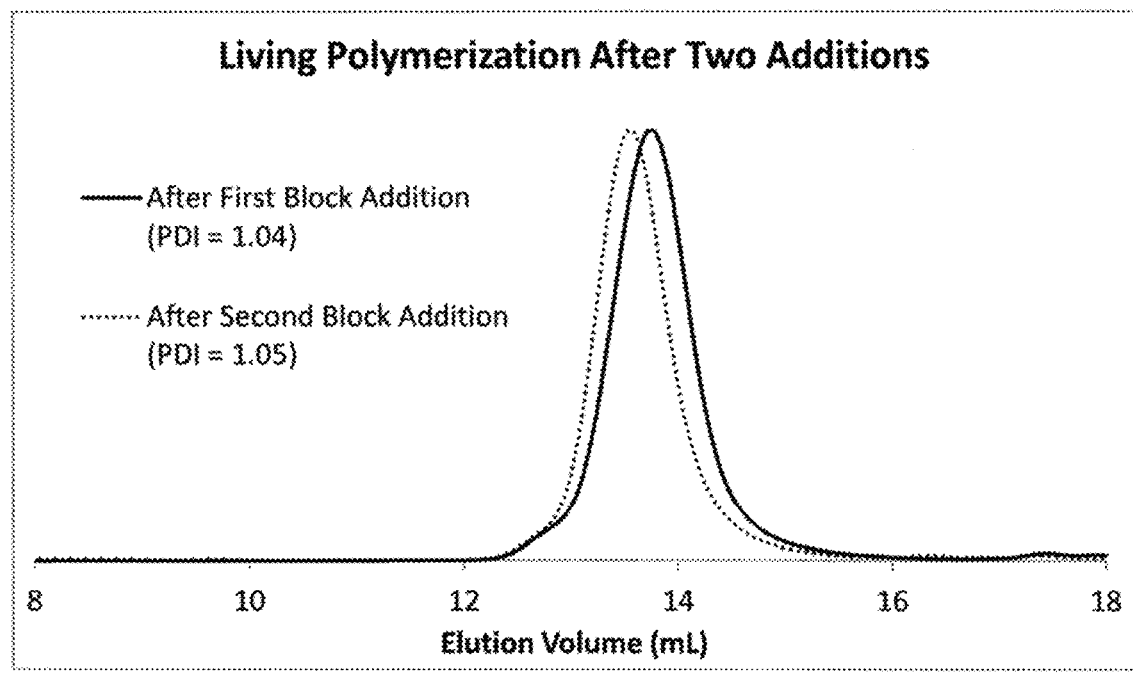
FIG. 3 is a gel permeation chromatogram of a chain extension experiment.
Figure 4:
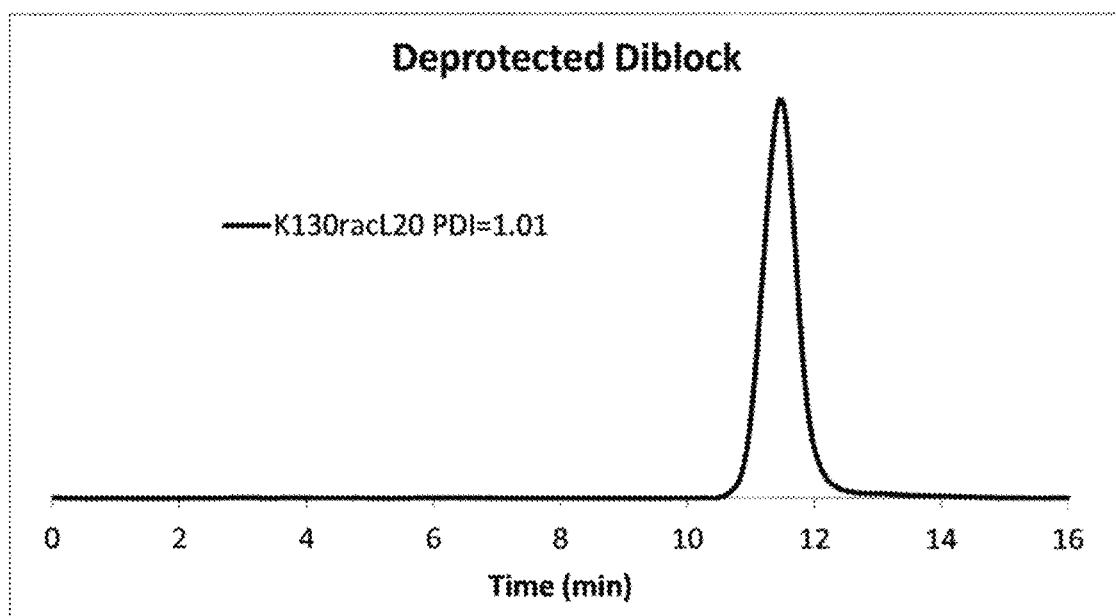
FIG. 4 is a gel permeation chromatogram of a representative deprotected diblock copolypeptide.
Figure 5A:
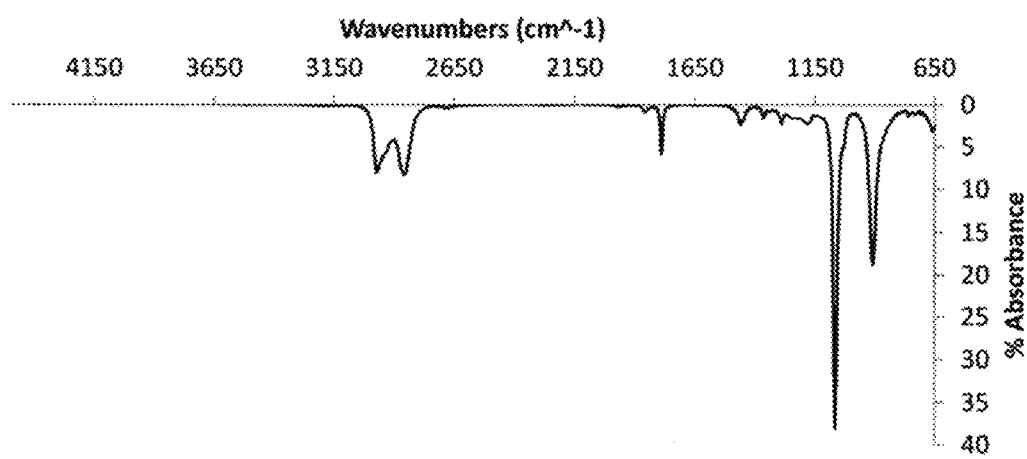
FIGS. 5A and 5B show attenuated total reflectance fourier-transform infrared (ATR-IR) interferograms of Leucine N-carboxy anhydride (NCA) and TFA-Lysine NCA monomers, respectively.
Figure 5B:
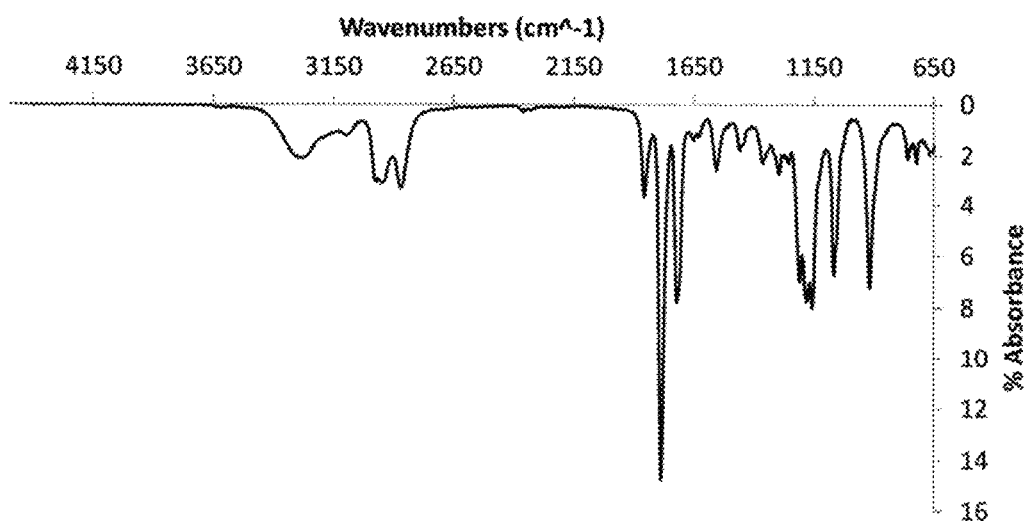
Figure 6A:
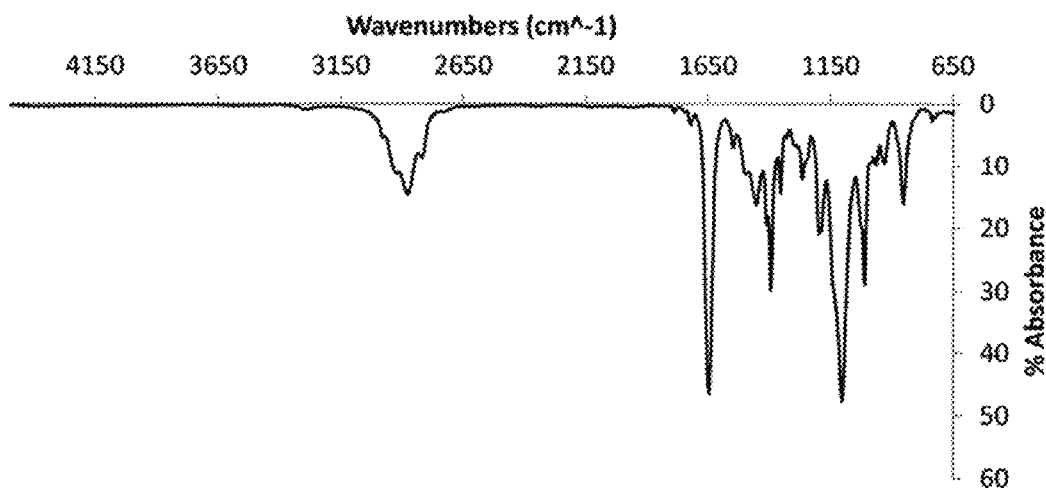
FIGS. 6A and 6B show attenuated total reflectance fourier-transform infrared (ATR-IR) interferograms of a crude reaction mixture and a completed polymerization, respectively.
Figure 6B:
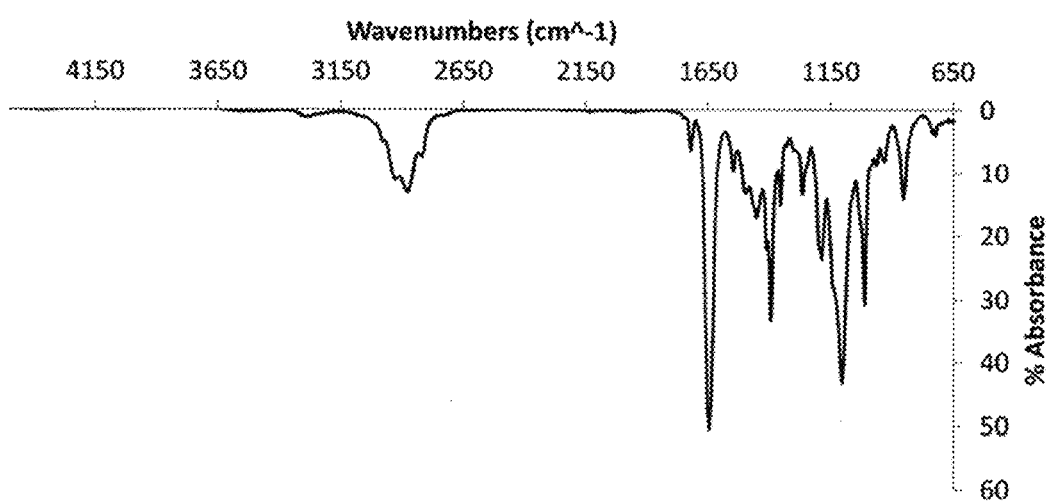
Figure 7A:
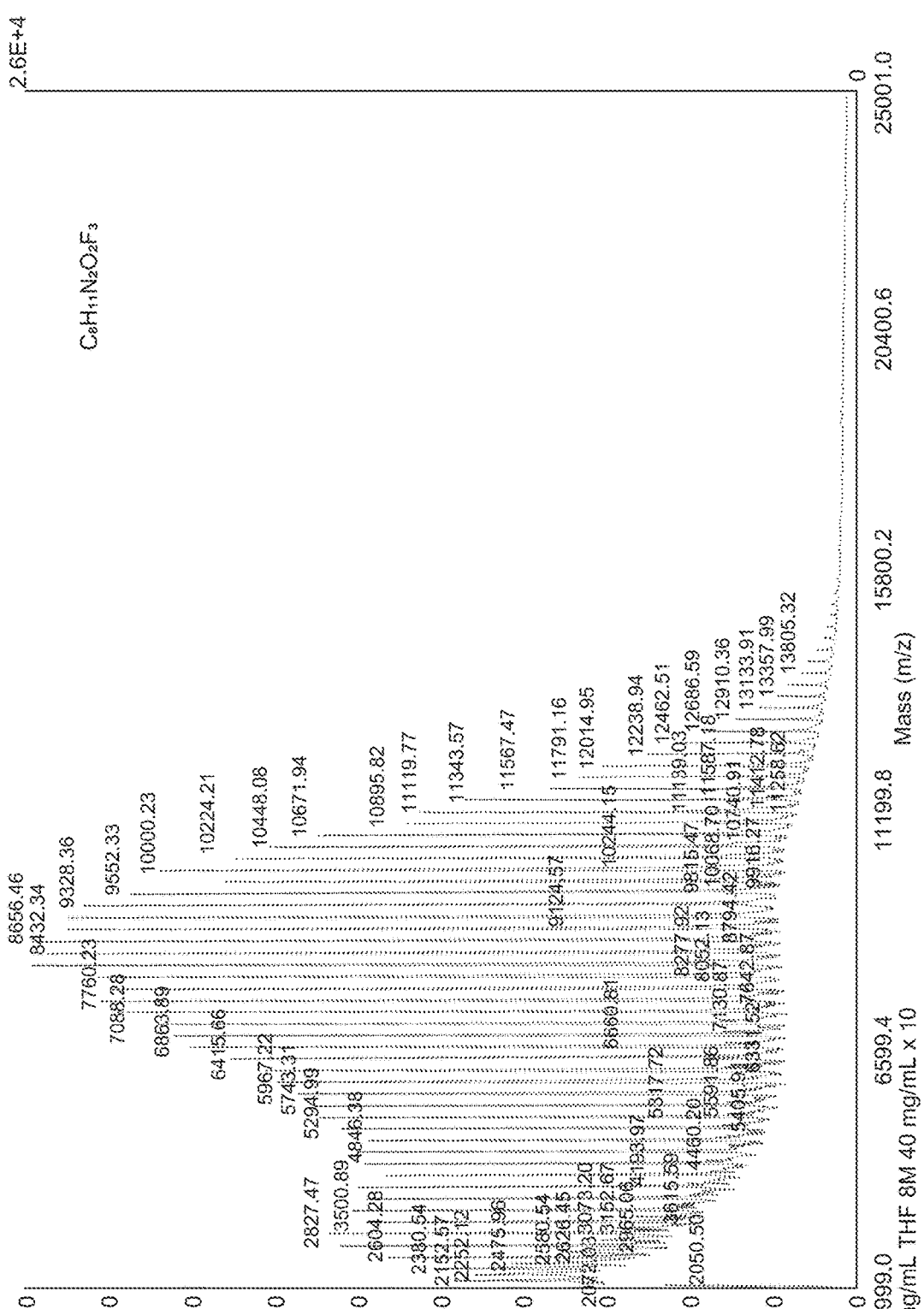
FIGS. 7A and 7B show a matrix-assisted laser desorption ionization (MALDI) mass spectrum of a representative peptide and an expanded view of a portion of that MALDI spectrum, respectively.
Figure 7B:
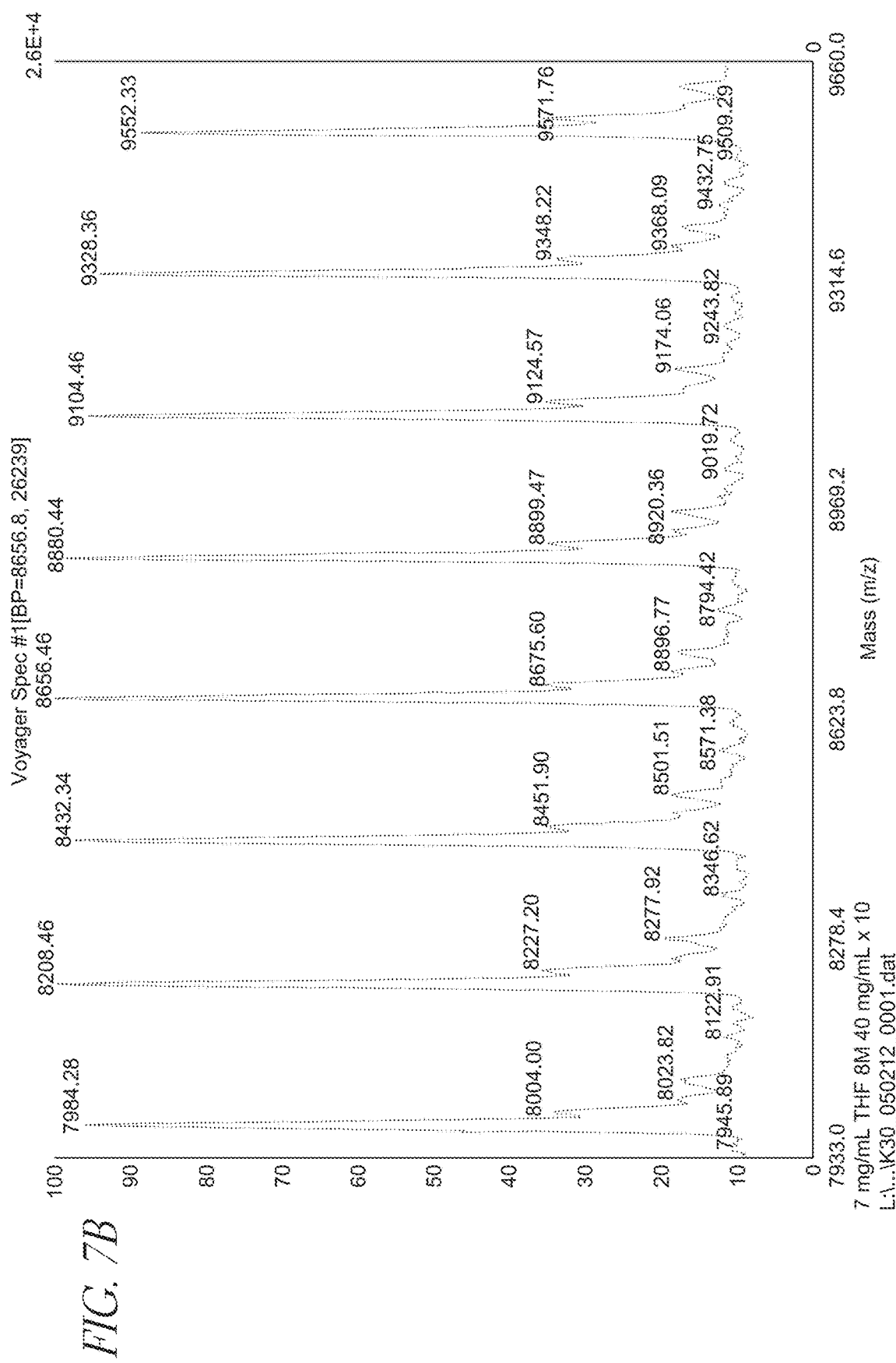
Figure 8:
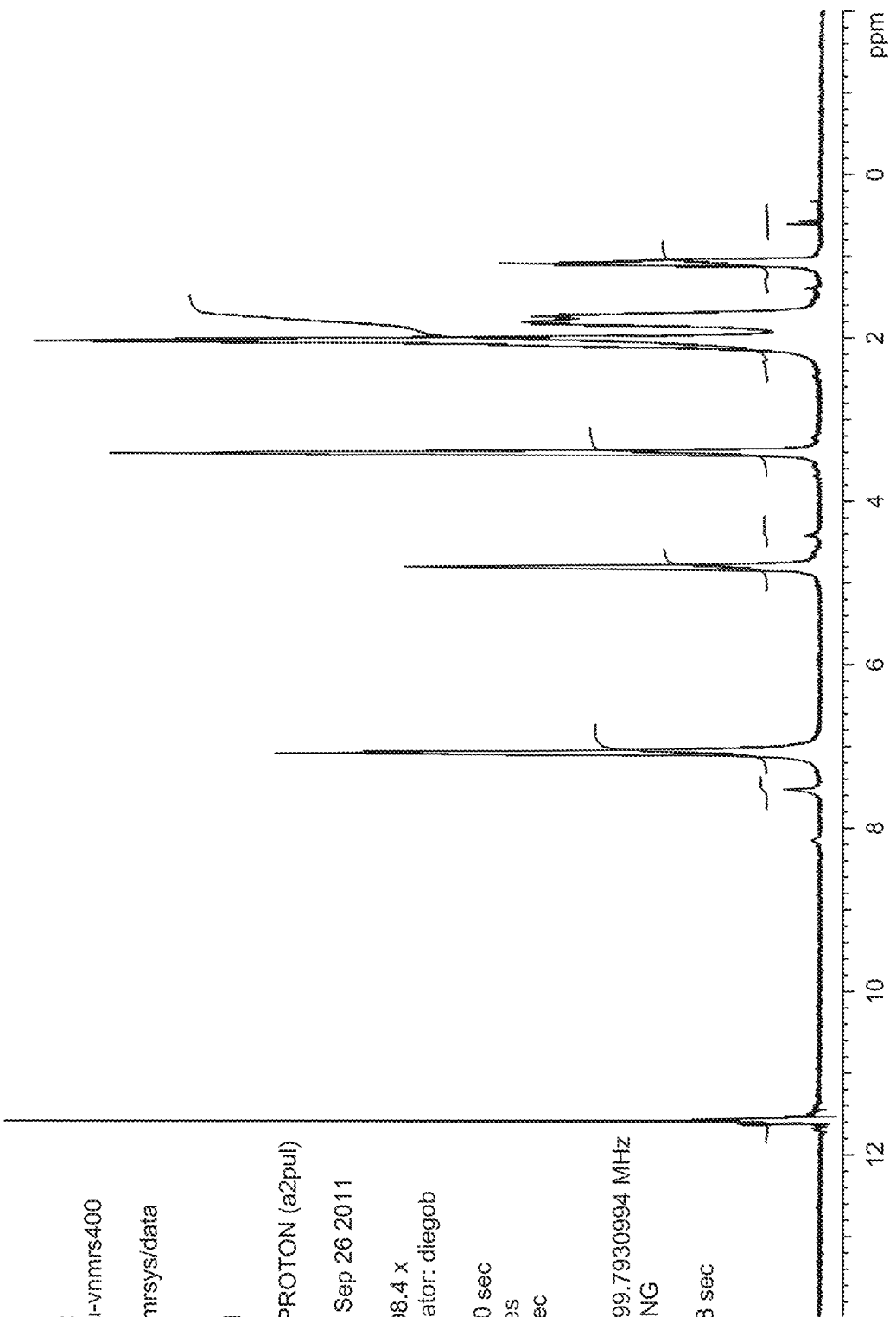
FIG. 8 shows a liquid proton nuclear magnetic resonance ($H^1$—NMR) spectrum of a representative deprotected copolypeptide in d-TFA.
Figure 9:
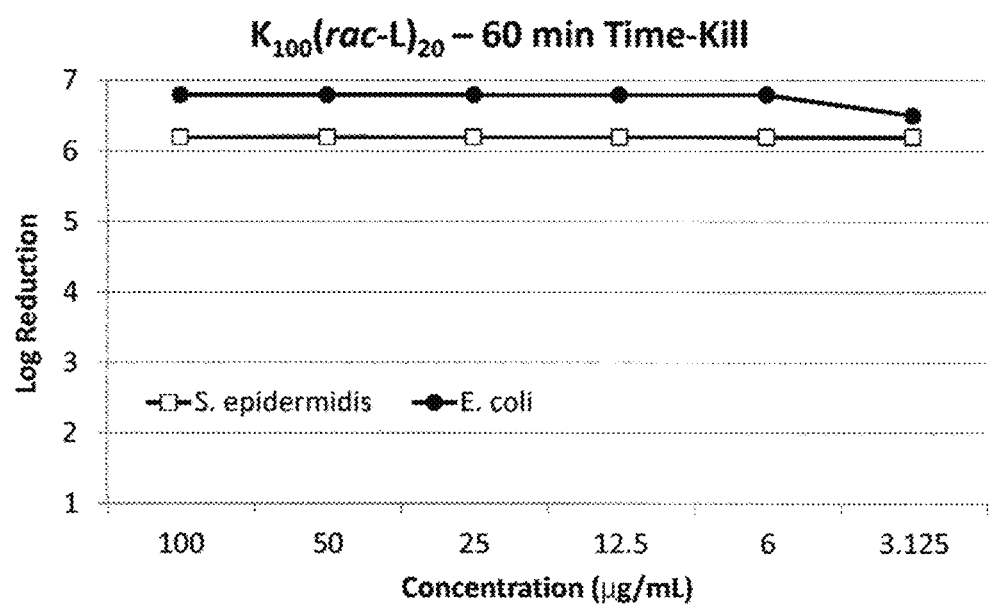
FIG. 9 shows an in vitro antimicrobial time-kill assay (60 min) against *S. epidermidis* (RMA 18291), and *E. coli* (ATCC 25922) using $K_{100}(\text{rac-L})_{20}$ (SEQ ID NO: 12).
Figure 10:
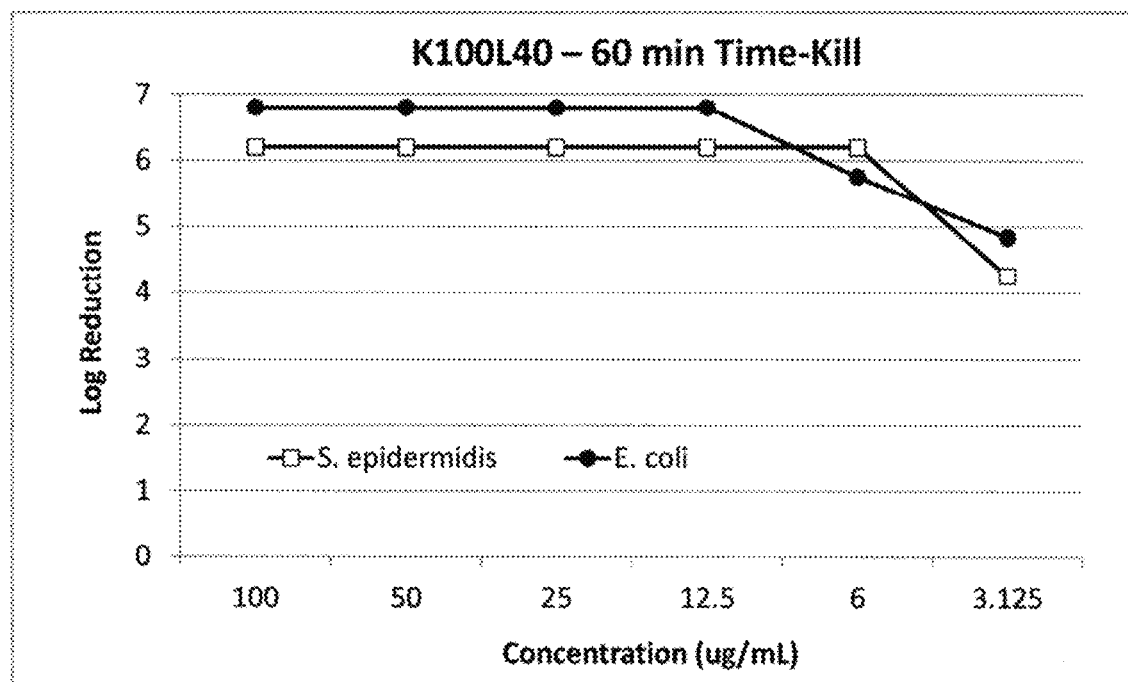
FIG. 10 shows an in vitro antimicrobial time-kill (60 min) against *S. epidermidis* (RMA 18291), and *E. coli* (ATCC 25922) using $K_{100}L_{40}$ (SEQ ID NO: 19).

In accordance with embodiments of the invention, an aqueous composition that includes a mixture of an antimicrobial cationic polypeptide and a second pharmaceutically-acceptable polymer is used in the treatment and/or prevention of infections that occur when our natural barriers of defense are broken. This novel composition can display two functions: direct antimicrobial activity and barrier activity. Embodiments of the invention addresses one or more weaknesses of previous antimicrobials described above. Notably, the inventors began with the recognition that most of the previous antiseptics and antibiotics were based on antimicrobial activity in solution with the microbes in suspension (MIC assays), a method that could lead away from effectiveness in tissues. By contrast, the inventors focused on the design and selection of agents for broad antimicrobial activity, especially at tissue surfaces and in the terrain ("cracks and crevices") of wounds. This includes the formation of a barrier containing cationic (positively charged) elements that can inhibit the movement of certain substances or cells that display anionic elements (e.g., microbes). In one embodiment, the synthetic cationic polypeptides of these compositions contain at least one cationic segment and at least one hydrophobic segment, are comprised substantially of natural amino acids, and are broadly antimicrobial (i.e., against gram positive and gram negative bacteria). They can also be designed to self-assemble, based in part on the interaction of their hydrophobic segments. Further, synthetic polypeptides are formulated with a second pharmaceutically-accepted polymer to provide a composition that is directly antimicrobial and that effectively coats tissues. These mixtures may also display hemostatic properties. In some embodiments, the second pharmaceutically acceptable polymer is not a polyethylene glycol (PEG).

Embodiments of the invention may be used alone or in combination with other materials that provide similar or complementary activities.

Synthetic cationic polypeptides.

A variety of synthetic cationic polypeptides can be used in the aqueous compositions described herein. In an embodiment, the synthetic cationic polypeptide comprises a segment of recurring units or residues of positively charged amino acids (e.g. lysine, arginine) and another segment of recurring units or residues of hydrophobic amino acids (e.g. leucine, isoleucine, valine, alanine). Examples include copolypeptides composed of a segment or block of one or more recurring lysine amino acids and a segment or block of one or more recurring leucine amino acids with the overall structure of $K_xL_y$ (FIGS. 1A and 1B). In various embodiments, one or more of the synthetic cationic polypeptide(s) comprise a segment having a chain length of at least 40 amino acid residues. In various embodiments, the synthetic cationic polypeptide(s) comprises substantially all natural amino acid subunits. In some embodiments, the synthetic cationic polypeptide(s) is characterized by at least one segment containing at least five consecutive cationic amino acid residues and at least one segment containing at least five consecutive hydrophobic amino acid residues. For example, in some cases, the polypeptides include one or more segments comprising at least 5 consecutive recurring lysine amino acid units and one or more segments comprising at least 5 consecutive hydrophobic recurring amino acids (e.g., leucine). In some cases, cationic polypeptides may be relatively long-chain molecules having lysine blocks containing 50 to 200 or more lysine amino acid residues. Examples of synthetic cationic polypeptides include $K_{50}(rac\text{-}L)_{10}$ (SEQ ID NO: 1), $K_{50}(rac\text{-}L)_{20}$ (SEQ ID NO: 2), $K_{50}(rac\text{-}L)_{30}$ (SEQ ID NO: 3), $K_{50}(rac\text{-}L)_{40}$ (SEQ ID NO: 4), $K_{50}(rac\text{-}L)_{50}$ (SEQ ID NO: 5), $K_{50}L_{10}$ (SEQ ID NO: 6), $K_{50}L_{20}$ (SEQ ID NO: 7), $K_{50}L_{30}$ (SEQ ID NO: 8), $K_{50}L_{40}$ (SEQ ID NO: 9), $K_{50}L_{50}$ (SEQ ID NO: 10), $K_{100}(rac\text{-}L)_{10}$ (SEQ ID NO: 11), $K_{100}(rac\text{-}L)_{20}$ (SEQ ID NO: 12), $K_{100}(rac\text{-}L)_{30}$ (SEQ ID NO: 13), $K_{100}(rac\text{-}L)_{40}$ (SEQ ID NO: 14), $K_{100}(rac\text{-}L)_{50}$ (SEQ ID NO: 15), $K_{100}L_{10}$ (SEQ ID NO: 16), $K_{100}L_{20}$ (SEQ ID NO: 17), $K_{100}L_{30}$ (SEQ ID NO: 18), $K_{100}L_{40}$ (SEQ ID NO: 19), $K_{100}L_{50}$ (SEQ ID NO: 20), $K_{200}(rac\text{-}L)_{10}$ (SEQ ID NO: 21), $K_{200}(rac\text{-}L)_{20}$ (SEQ ID NO: 22), $K_{200}(rac\text{-}L)_{30}$ (SEQ ID NO: 23), $K_{200}(rac\text{-}L)_{40}$ (SEQ ID NO: 24), $K_{200}(rac\text{-}L)_{50}$ (SEQ ID NO: 25), $K_{200}L_{10}$ (SEQ ID NO: 26), $K_{200}L_{20}$ (SEQ ID NO: 27), $K_{200}L_{30}$ (SEQ ID NO: 28), $K_{200}L_{40}$ (SEQ ID NO: 29), $K_{200}L_{50}$ (SEQ ID NO: 30) (FIGS. 2A and 2B). Other synthetic cationic polypeptides (e.g. with longer or shorter lysine segments and longer or shorter leucine segments) are also envisioned. Also, this invention includes other synthetic cationic polypeptides where the cationic segments can include other amino acids, such as arginine, and hydrophobic blocks that can contain one or more hydrophobic amino acids, including but not limited to leucine, alanine, valine, and/or isoleucine. In some cases, one or more of the segments may have a random sequence of amino acids, including hydrophobic and hydrophilic amino acids.

Examples of synthetic cationic polypeptides include those described in U.S. Pat. Nos. 6,680,365; 6,632,922; 6,686,446; 6,818,732; 7,329,727; US Published Patent Application No. 2008/0125581; and US Published Patent Application No. 2011/048869. The aforementioned patents and patent applications are hereby incorporated herein by reference, and particularly for the purpose of describing synthetic cationic polypeptides and method of making them.

Methods of manufacturing synthetic cationic polypeptides that have exceptionally narrow polydispersities with high reproducibility have been developed, and such polymers can be made to various specifications to suit the needs of the antimicrobial activity and the barrier formation. For example, by combining high quality α-amino acid N-carboxy anhydrides (NCAs) in anhydrous solvents with a benzyl amine initiator, a high quality block copolypeptide is synthesized. These polymers then undergo deprotection and purification to yield the final product.

Several analytical techniques have been developed and refined to both monitor the synthesis of the peptides and to analyze the resulting polymeric products for size, properties and residual impurities. Infrared spectroscopy may be used to monitor the progress of the reaction, while Size Exclusion Gel Permeation Chromatography may be used to monitor the growth and status of the polymer at various stages of the process. Other analytical techniques such as nuclear magnetic resonance spectroscopy (NMR), matrix assisted laser desorption ionization mass spectroscopy (MALDI-MS), and inductively coupled plasma mass spectroscopy (ICP-MS) may be used, e.g., as additional quality control tests to ensure consistent reproducibility and purity (FIG. 3-8).

Figure 13:
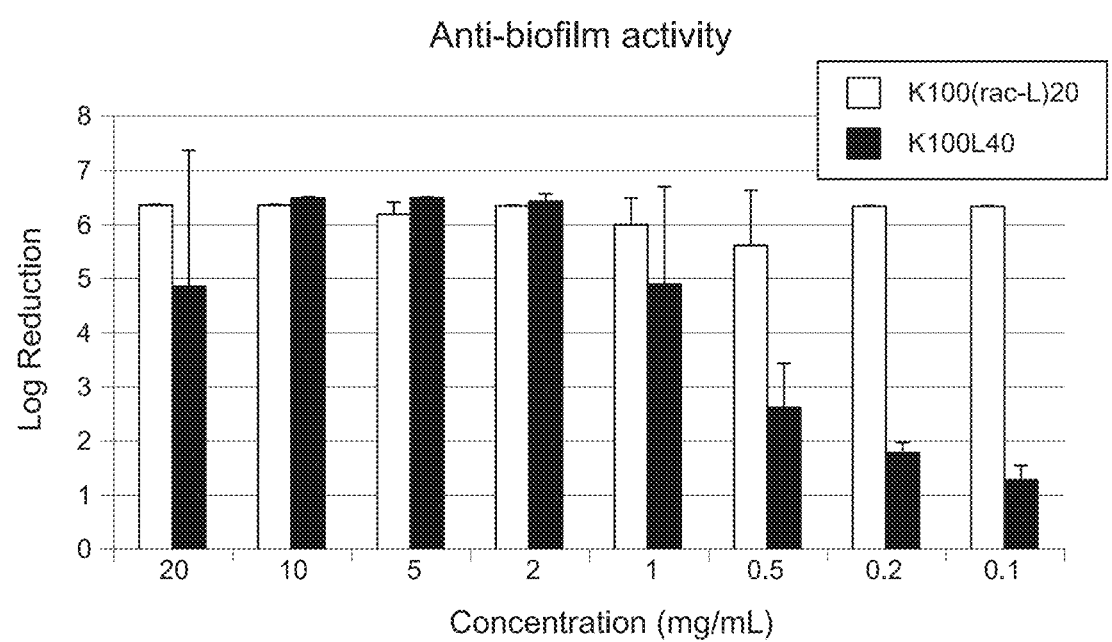
FIG. 13 shows that $K_{100}(\text{rac-L})_{20}$ (SEQ ID NO: 12) and $K_{100}L_{40}$ (SEQ ID NO: 19) at concentrations of 0.1-20 mg/mL are effective against *P. aeruginosa* biofilms in vitro (24 hour contact time).
Figure 14A:
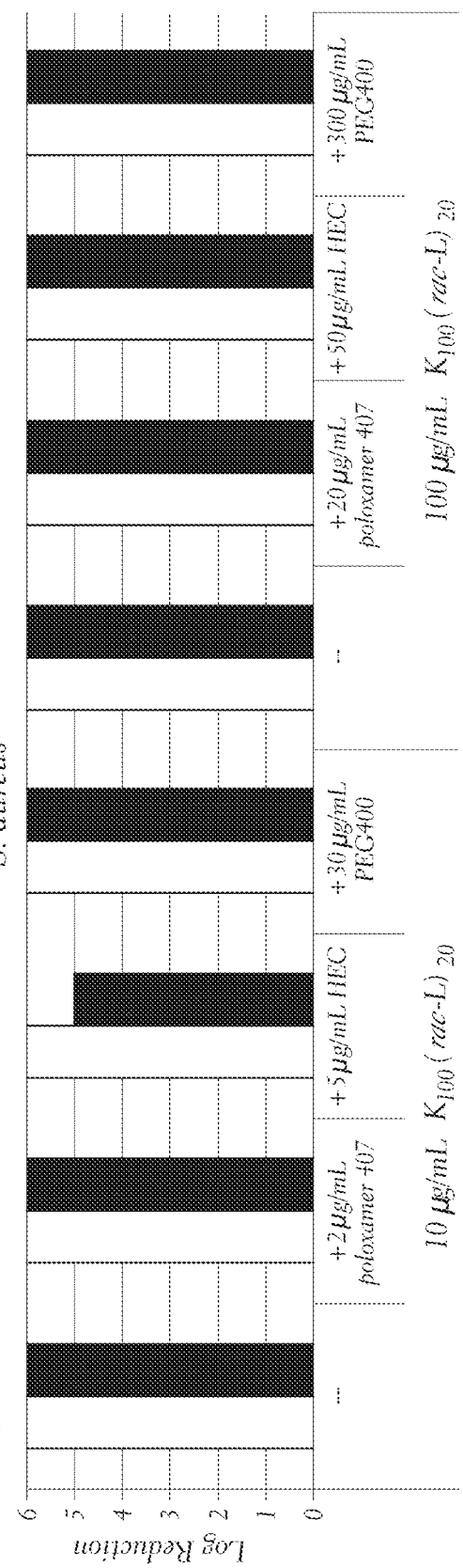
FIGS. 14A and 14B show in vitro antimicrobial time-kill assays against *S. aureus* (29213), and *P. aeruginosa* (27853), respectively, after 5 and 60 min, using $K_{100}(\text{rac-L})_{20}$ (SEQ ID NO: 12) at concentrations of 10 and 100 µg/mL with other ratios of excipients: 5:1 $K_{100}(\text{rac-L})_{20}$ (SEQ ID NO: 12):Poloxamer 407, 2:1 $K_{100}(\text{rac-L})_{20}$ (SEQ ID NO: 12): HEC, and 1:3 $K_{100}(\text{rac-L})_{20}$ (SEQ ID NO: 12):Peg 400.
Figure 14B:
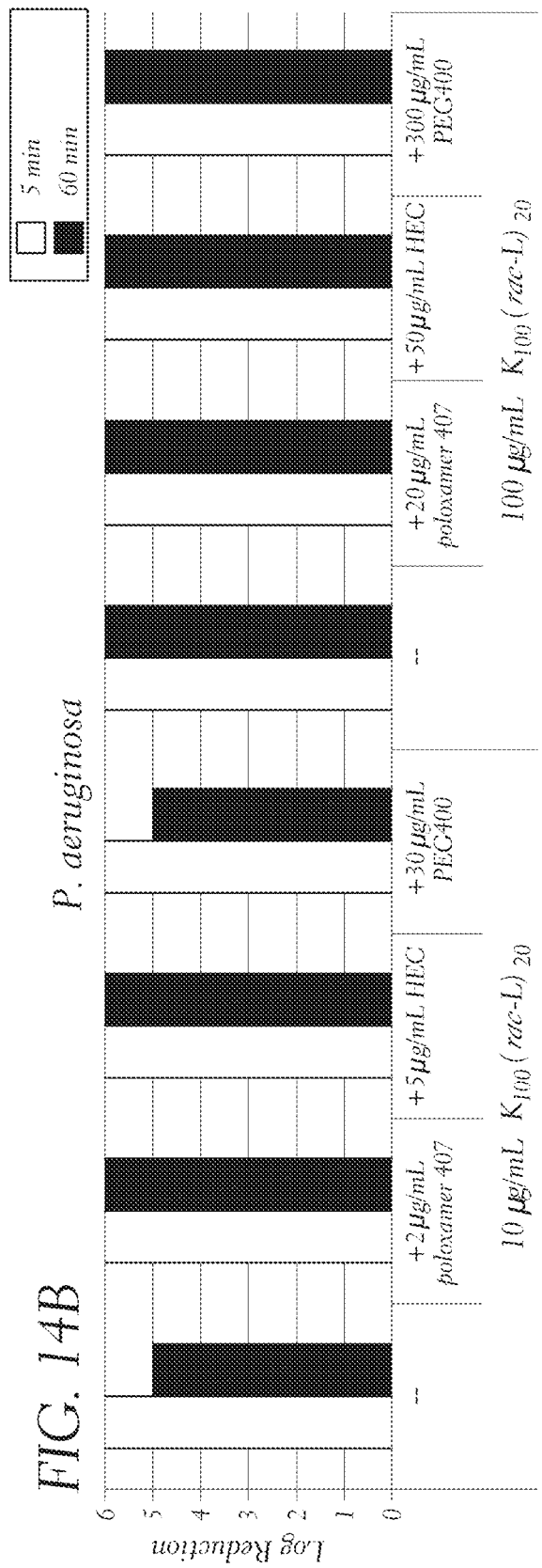
Figure 15:
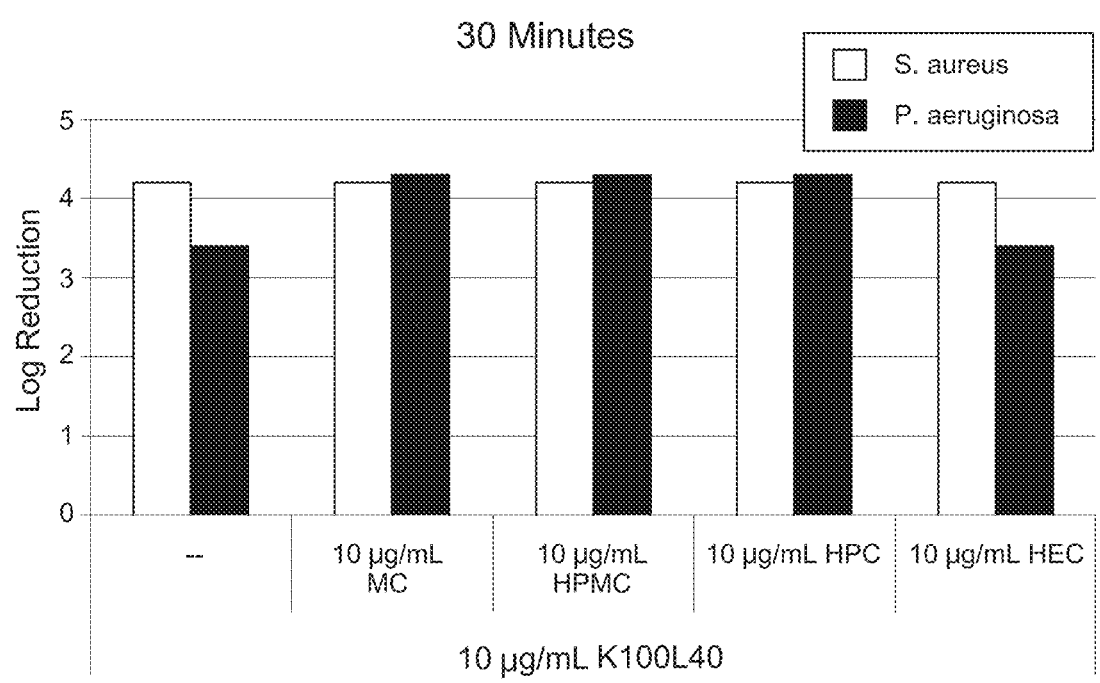
FIG. 15 shows an in vitro antimicrobial time-kill assay against *S. aureus* (29213) after 30 min, using $K_{100}L_{40}$ (SEQ ID NO: 19) (10 µg/mL) alone and in combination with cellulose ethers (methyl cellulose (MC), hydroxypropylmethyl cellulose (HPMC), hydroxypropyl cellulose (HPC), and hydroxyethyl cellulose (HEC)) at a 1:1 ratio.
Figure 17A:
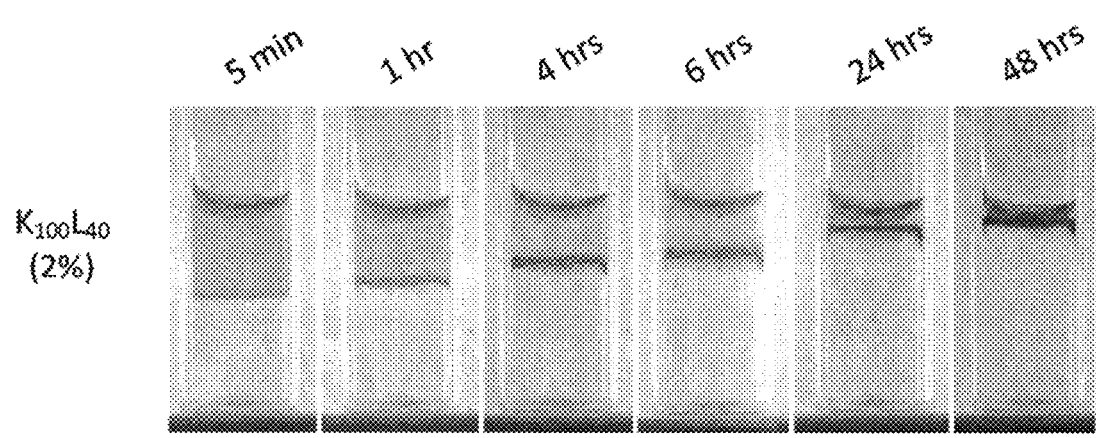
FIGS. 17A and 17B show barrier assays using $K_{100}L_{40}$ (SEQ ID NO: 19) and polyethylene glycol (PEG), respectively.
Figure 17B:
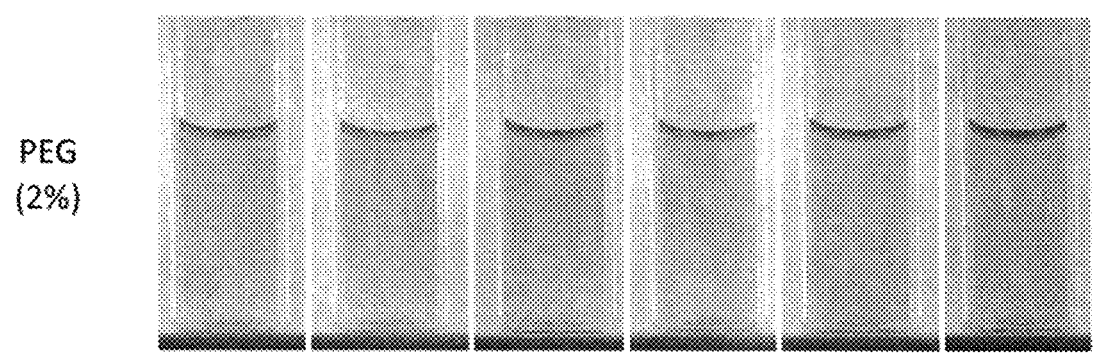
Figure 18:
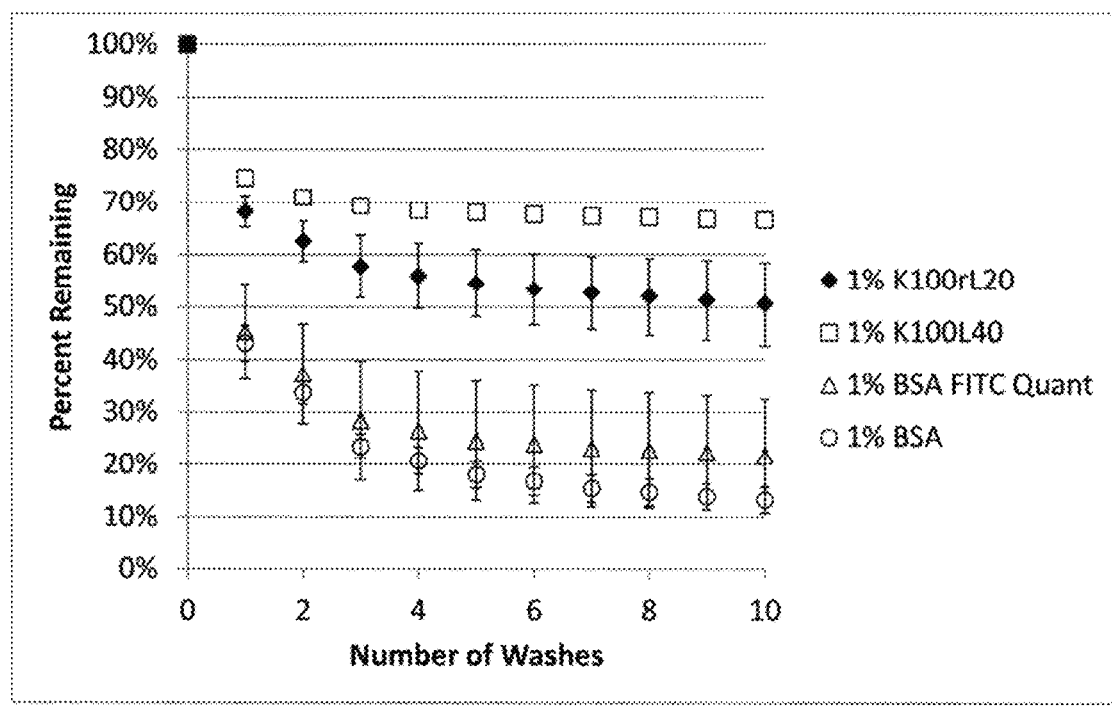
FIG. 18 shows a synthetic cationic polypeptide binding to Vitroskin©, a synthetic tissue analogue. A substantial portion of applied FITC-labeled copolypeptides were shown to remain associated with Vitroskin©, as demonstrated using 1% solutions of FITC-$K_{100}$(rac-L)$_{20}$ (SEQ ID NO: 12) and FITC-$K_{100}L_{40}$ (SEQ ID NO: 19). By comparison, the majority of labeled BSA was removed by washing. The % remaining was determined using FITC fluorescence ($\lambda_{exc}$=495 nm, $\lambda_{em}$=521 nm) after 1-10 washes and calculated as 100% minus the percentage removed.
Figure 19:
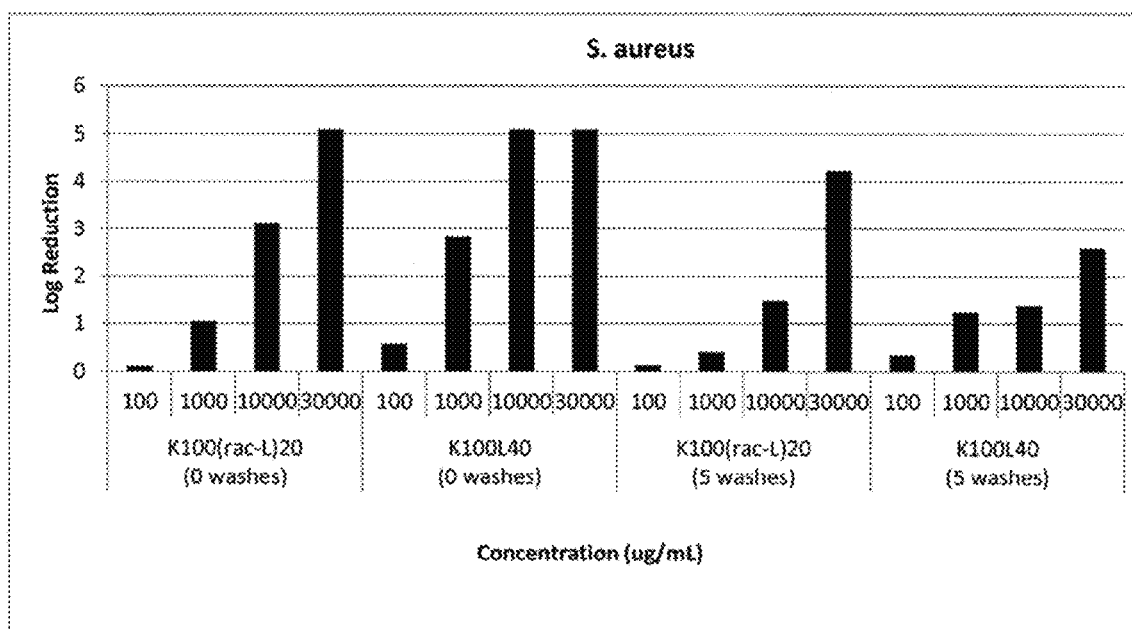
FIG. 19 shows in vitro antimicrobial activity of $K_{100}$(rac-L)$_{20}$ (SEQ ID NO: 12) and $K_{100}L_{40}$ (SEQ ID NO: 19) (100-3000 µg/mL) on a Vitroskin© surface against *S. aureus* after 0 and 5 washes (5×1 mL). Each 3 cm×3 cm piece of Vitroskin© was incubated with *S. aureus* for 60 min.

Synthetic cationic polypeptides can be designed to demonstrate broad-based antimicrobial activity (see US Published Patent Application No. 2011/048869). A synthetic cationic polypeptide is considered to have antimicrobial activity if it provides greater than 3 logs killing of *Staphylococcus epidermidis* and *Escherichia coli* in a standard 60 minute time-kill assays at a synthetic cationic polypeptide concentration of 1.0 mg/mL or less. In an embodiment, the synthetic cationic polypeptide has an antimicrobial activity that provides greater than 3 logs killing of *Staphylococcus epidermidis* and *Escherichia coli* in a standard 60 minute time-kill assays at a synthetic cationic polypeptide concentration of 100 μg/mL or less. As shown in FIGS. 9-12, embodiments of these synthetic cationic polypeptides demonstrate antimicrobial activity in vitro against both Gram-positive and Gram-negative bacteria. This activity is demonstrated in in vitro time-kill assays with the synthetic cationic polypeptides in aqueous media. Further, embodiments of synthetic cationic polypeptides demonstrated anti-biofilm activity in vitro, as depicted in FIG. 13. It is likely that these effects can be explained in part by the cationic polypeptides binding to the anionic charges present in the matrix of the biofilm. In addition, the surfactant-like activity of the synthetic cationic polypeptides may contribute to the anti-biofilm effect. It is also recognized that the inventive compositions may change the structure and/or charge of biofilms, allowing other agents (e.g., locally applied or systemically applied antibiotics) to penetrate the biofilm, thereby enhancing activity.

Mixtures of synthetic cationic polypeptides and other polymers can retain antimicrobial activity in vitro. The second pharmaceutically-acceptable polymer is different from the one or more synthetic, cationic polypeptide(s)

having antimicrobial activity. In an embodiment, the second pharmaceutically-acceptable polymer has little or no antimicrobial activity itself. For example, in an embodiment, the antimicrobial activity of second pharmaceutically-acceptable polymer is less than 10% of the antimicrobial activity of the synthetic, cationic polypeptide(s).

The individual amounts of the synthetic, cationic polypeptide(s) and the second pharmaceutically-acceptable polymer in the aqueous composition are at least about 100 µg/mL, and can be higher, e.g. about 1 mg/mL, about 5 mg/mL, or about 10 mg/mL, or about 20/ml, or about 40 mg/ml or higher. The amount of the second pharmaceutically-acceptable polymer in the aqueous composition is at least about 10% by weight, based on the weight of the one or more synthetic, cationic polypeptide(s), and may be higher, e.g., at least about 20% by weight, at least about 30% by weight, or at least about 50% by weight, same basis. The synthetic, cationic polypeptide(s) and the second pharmaceutically-acceptable polymer in the aqueous composition are selected such the polymers are mutually miscible. As noted above, the synthetic, cationic polypeptide(s) with antimicrobial activity and the second pharmaceutically-acceptable polymer are considered mutually miscible if at least about 90% of the polymeric components remain mutually soluble 24 hours after mixing and maintaining at room temperature in water at a concentration of each polymer of 1 mg/mL, upon visible examination. Surprisingly, such mutual miscibility of the water, synthetic, cationic polypeptide(s) and the second pharmaceutically-acceptable polymer can be achieved, despite the expectation of phase separation due to the typical mutual incompatibility of polymers in aqueous solution at the 1 mg/mL concentrations and molecular weights described herein. The aqueous compositions described herein can be prepared by intermixing the individual polymeric components with water, e.g., at room temperature with stirring, using ordinary mixing methods known to those skilled in the art.

Example 1

As depicted in FIGS. 14A-16, embodiments of synthetic cationic polypeptides were shown to retain substantially all of their antimicrobial activity in the presence of other pharmaceutically-acceptable polymers, as demonstrated by in vitro time-kill assays against *S. aureus, S. epidermidis, P. aeruginosa*, and *E. coli*. In these studies, a variety of cellulose-based second polymers were evaluated. As shown in FIGS. 11 and 13, other studies demonstrated retained antimicrobial activity in in vitro the presence of other pharmaceutically-acceptable (polymeric surfactants). In an embodiment, the antimicrobial activity of the aqueous composition is greater than 3 logs killing of *Staphylococcus epidermidis* and *Escherichia coli* in standard 60 minute time-kill assays at a synthetic cationic polypeptide(s) concentration of 100 µg/mL or less. In another embodiment, the aqueous composition is further characterized by the ability to disrupt or inhibit a biofilm in vitro at a total polymer concentration of 40 mg/ml or less.

Mixtures of synthetic cationic polypeptides and other polymers can exhibit enhanced physical and viscoelastic properties in vitro. In developing compositions for use in patients, the need to maintain antimicrobial activity while enhancing volume, tissue coverage areas, and/or biocompatibility has been recognized. Various synthetic cationic polypeptides have been combined with other pharmaceutically-acceptable polymers in a way to retain at least about 80% (e.g., at least 90%) of the antimicrobial activity of the synthetic cationic polypeptides and, in preferred embodiments, also enhance tissue coverage. It is believed that the amphiphilic nature of the synthetic cationic polypeptides and their self-assembly in aqueous solution induce stable phase-separated (collapsed or solvated) dispersions of hydrophobic and hydrated hydrophilic material. In some embodiments, it is believed that the chain length of the copolypeptides (e.g., degree of polymerization or n>50) provides a network of partially collapsed pockets of hydrophobicity that slow down solute and solvent diffusion. The barrier nature of the materials is a product of the ability of the materials to trap and slow down water mobility, and by consequence dramatically slow down the passage of any solute or particle present in water. The length of the polypeptide strongly influences the barrier properties (e.g., by drastically reduced diffusion). Therefore, selection of a second polymer for mixing with the synthetic cationic peptide(s) should be undertaken carefully to avoid disruption of influential biophysical parameters and to achieve mutual solubility in the aqueous composition. Those skilled in the art can use routine experimentation guided by the teachings provided herein to select the polymeric components and amounts to form the aqueous compositions described herein.

The properties of the aqueous compositions described herein can be tuned by controlling the ratio of the amount of the cationic polypeptide to the second pharmaceutically-acceptable polymer(s). Non-limiting examples of these second polymers may include celluloses (e.g, hydroxyethylcellulose (HEC), hydroxypropylcellulose (HPC), hydroxymethylcellulose (HMC)), alginates, collagens, polymeric surfactants, polyethylene glycols, polyvinyl alcohols, polyurethanes, polyvinyl pyrolidinones (PVP), fibrin(ogen), or blood or tissue proteins. In some embodiments, the second pharmaceutically acceptable polymer is not a polyethylene glycol (PEG). It is believed that the barrier of the composition is in dynamic equilibrium with its individual components, at least one of which is also antimicrobial. The leaching of aggregates may be an advantage because the shed material may increase the effective surface area of the barrier which may increase the effectiveness of the interaction between microbes and the barrier material (FIG. 17A-19). Barrier properties of the materials can be further enhanced by the synergistic effect of polar biopolymers that further crosslink the self-assembled co-polypeptide matrix. By formulating with different biopolymers the flow and mechanical characteristics of the materials, as well as the strength of the barrier can be adjusted and controlled.

Example 2

Figure 20A:
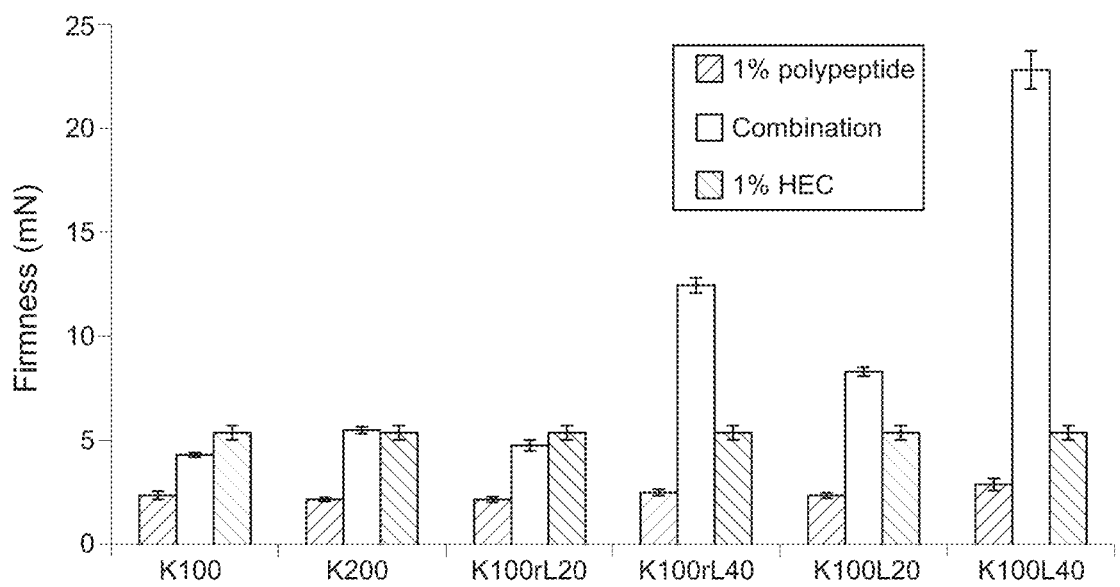
FIGS. 20A and 20B show A) firmness values for mixtures of 1% solutions of synthetic cationic polypeptides with 1% hydroxyethyl cellulose (HEC, Natrosol HHX) in water (FIG. 20A); and B) work of adhesion values for mixtures of 1% solutions of copolypeptides with 1% hydroxyethyl cellulose (HEC, Natrosol HHX) in water (FIG. 20B).
Figure 20B:
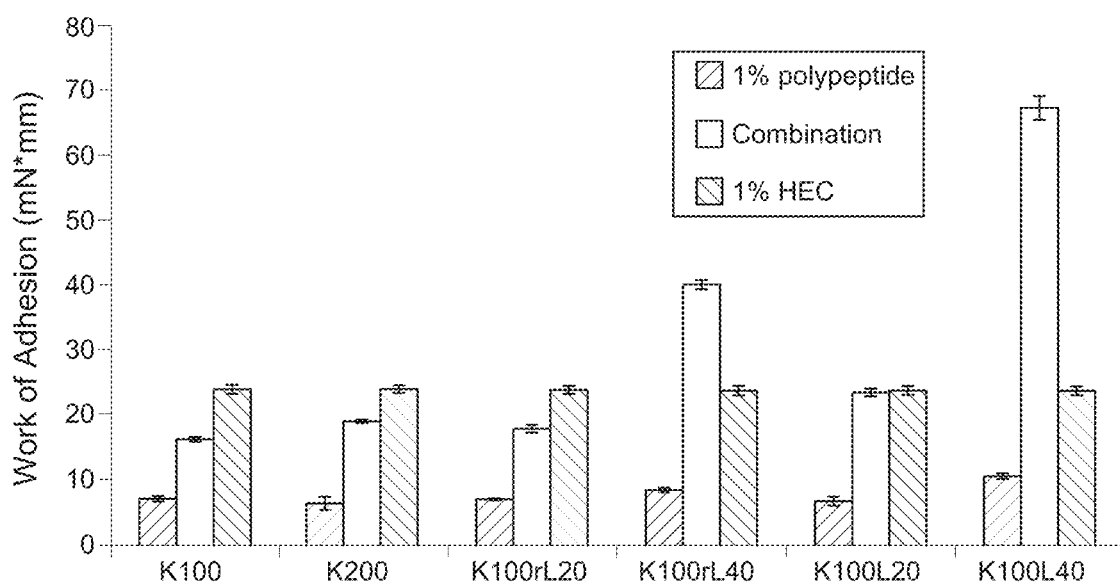

A texture analysis profile has been used to determine the effects of block copolypeptide composition and hydrophobic enantiopurity on the mechanical properties of the block copolypeptide/HEC mixtures (FIGS. 20A and 20B). Measurement of firmness values for individual components indicated that a 1% (w/w) solution of $K_{100}L_{40}$ (SEQ ID NO: 19) in water had a firmness of 2.94+/−0.25 mN and a solution of 1% (w/w) HEC in water demonstrated a firmness of 5.38+/−0.32 mN (FIG. 21 (Table 5)). Mixing 1% (w/w) $K_{100}L_{40}$ (SEQ ID NO: 19) and 1% HEC (w/w) together resulted in a substantial increase in firmness, to a value of 22.77+/−0.90 mN. This corresponds to an interaction parameter value of 14.45 mN and an overall increase of over 170% over what would be expected from the additive contributions of the individual components. As shown in FIG. 20*b*, a similar trend was observed for adhesiveness. By comparison, the combination of the diblock copolypeptide $K_{100}$(rac-L)$_{40}$ (SEQ ID NO: 14) (containing a racemic hydrophobic block) at 1% (w/w) and HEC at 1% (w/w) concentration also demonstrated enhanced firmness and adhesiveness; however, the increase was not as pronounced as with $K_{100}L_{40}$ (SEQ ID NO: 19), containing an enantiopure hydrophobic block. Hydrophobic block length was also shown to be influential. Mixtures of 1% (w/w) $K_{100}L_{20}$ (SEQ ID NO: 17) and 1% (w/w) HEC showed increased firmness over either biopolymer alone, but the effect was smaller than that of $K_{100}L_{40}$ (SEQ ID NO: 19). Interestingly, $K_{100}L_{20}$ (SEQ ID NO: 17) was antagonistic for work of adhesion. Further, $K_{100}$(rac-L)$_{20}$ (SEQ ID NO: 12), with its shorter racemic hydrophobic block, showed no effect. The lysine homopolypeptides, $K_{100}$ (SEQ ID NO: 31) and $K_{200}$ (SEQ ID NO: 32), also failed to enhance the firmness or adhesiveness of HEC alone, and in fact, appeared to demonstrate antagonistic activity.

Example 3

Figure 22A:
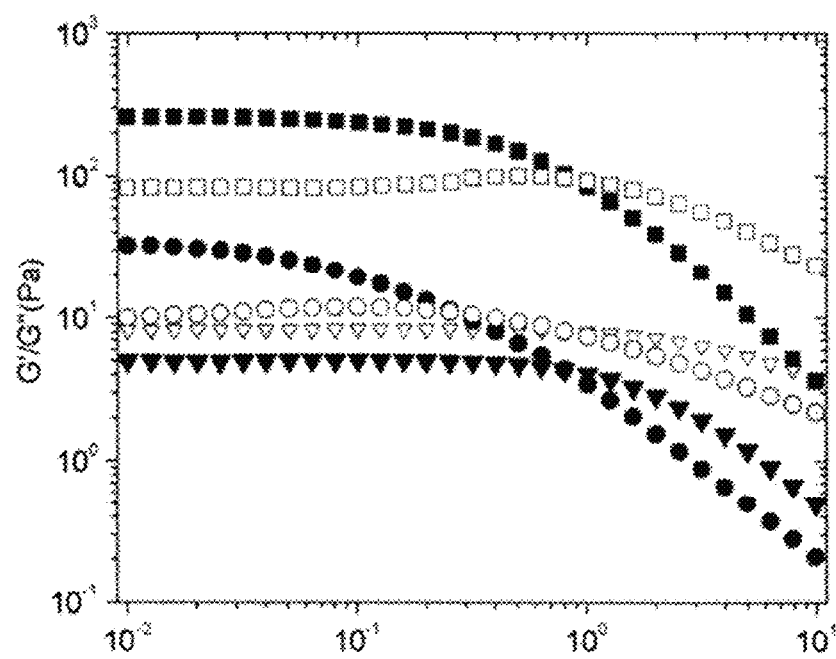
FIGS. 22A and 22B show A) Strain and B) frequency sweep of synergistic mixture of 1% $K_{100}L_{40}$ (SEQ ID NO: 19)/1% HEC and individual components at 1% in water, respectively. ■=1% $K_{100}L_{40}$ (SEQ ID NO: 19)/1% HEC, •=1% $K_{100}L_{40}$ (SEQ ID NO: 19), and ▼=1% HEC. G' values=filled symbols and G"=open symbols.
Figure 22B:
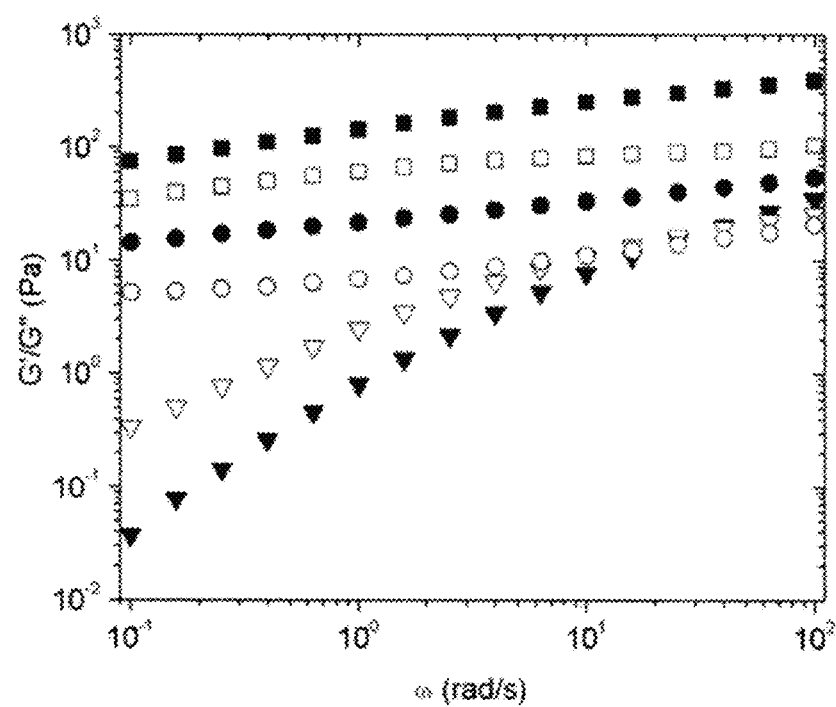

Rheological measurements further support the synergistic interactions between $K_{100}L_{40}$ (SEQ ID NO: 19) and HEC. In FIGS. 22A and 22B, effects are seen in both the oscillatory strain sweep and frequency dependent sweep. By itself, 1% (w/w) $K_{100}L_{40}$ (SEQ ID NO: 19) showed characteristics of a relatively brittle, weak gel. In strain sweep analysis, the brittle nature of the gel was observed by the breakdown of the gel network at low strain rates around $\gamma=0.01$; and frequency sweep analysis indicated the formation of a weak gel with an elastic modulus (G'=22 Pa at 1 rad/s). By comparison, 1% (w/w) HEC showed rheological properties more characteristic of a viscous fluid. Strain sweep analysis of a 1% HEC solution demonstrated a higher loss modulus (G") than elastic modulus (G') throughout all strain rates tested (FIG. 22A) and the frequency sweep also showed higher G" over G' values until higher frequencies (ca. 100 rad/s) were reached (FIG. 22B). Substantial changes in rheological properties were observed upon mixing 1% (w/w) $K_{100}L_{40}$ (SEQ ID NO: 19) with 1% (w/w) HEC. Notably, strain sweep analysis of the mixture showed an extension of the linear viscoelastic region by an order of magnitude showing a decrease in G' around $\gamma=0.1$. The frequency sweep showed a large, synergistic increase in the elastic modulus G'=141 Pa at 1 rad/s, which is a seven-fold increase over the elastic modulus of 1% (w/w) $K_{100}L_{40}$ (SEQ ID NO: 19) alone (G'=22 Pa).

The amounts and types of polymeric components in the aqueous compositions described herein can be selected to achieve various properties. In an embodiment, the aqueous composition is characterized by a barrier activity, as measured by a decrease in the diffusion rate of an anionic dye of more than 2 logs at a total polymer concentration of 40 mg/mL or less. In an embodiment, the aqueous composition is characterized by a storage modulus of at least 50 Pa at a total polymer concentration of less than 40 mg/mL. In an embodiment, the aqueous composition is characterized by a storage modulus of at least 50 Pa at a total polymer concentration of less than 40 mg/mL and an ability to pass through a 20 g needle using less than 60 N pressure. In an embodiment, the aqueous composition is characterized by an ability to pass through a 20 g needle and recover a minimum of 70% of its strength as measured by storage modulus within 10 minutes. Those skilled in the art can use routine experimentation guided by the teachings provided herein to select the polymeric components and amounts to form aqueous compositions having the properties described herein.

Example 4

Mixtures of synthetic cationic polypeptides and other polymers can exhibit enhanced antimicrobial activity in vivo. Notably, synthetic cationic polypeptides, as micellar solutions and as hydrogels, can be used to coat tissues in vivo (FIG. 23). This tissue coating may involve the binding of the cationic peptides, through charge interactions, to anionic charges displayed on damaged tissues (as well as anionic charges in bacterial biofilms). In addition, self-assembly and cross-linking may increase the amount of material that binds and coats a tissue (e.g. thinner or thicker coating) and therefore influence a variety of biological activities and responses.

Figure 24:
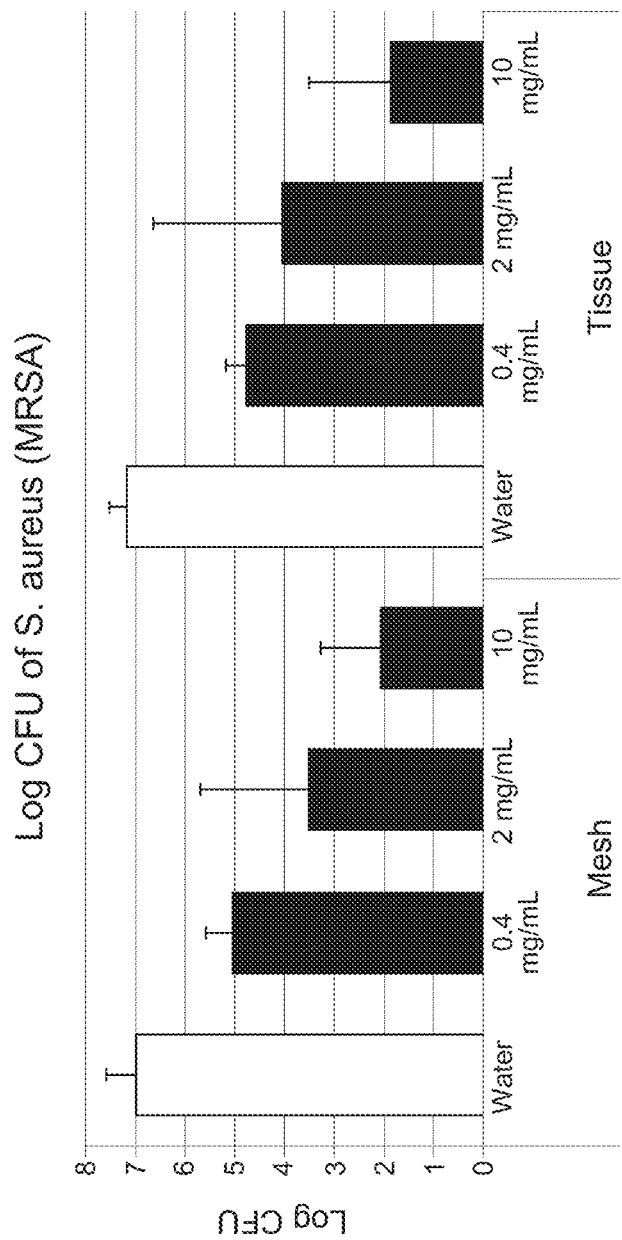
FIG. 24 shows the antimicrobial activity of $K_{100}$(rac-L)$_{20}$ (SEQ ID NO: 12) in a rodent infection model. Polypropylene mesh was inserted subcutaneously in rats followed by $10^7$ MRSA (33593). After 15 min., either 10, 2 or 0.4 mg/mL of $K_{100}$(rac-L)$_{20}$ (SEQ ID NO: 12) or water was added. After 2 days, implanted mesh and surrounding tissue were analyzed for MRSA bacterial counts.

As depicted in FIG. 24, these synthetic cationic polypeptides are antimicrobial when locally applied in vivo. In seeking to develop improved products for in vivo applications, it has been recognized that tissue binding and tissue coating properties of these materials may substantially affect their activities, including their antimicrobial properties, their anti-biofilm properties, and their effects on tissue adhesion formation and tissue remodeling. Molecular characteristics (e.g. length, charge, etc.) of the synthetic cationic polypeptides, as well as structures that they form in aqueous environments (e.g. micelles, sheets, fibrils, hydrogels) may affect tissue binding and tissue coating. It has also been recognized that mixing these synthetic cationic polypeptides with other polymers to form aqueous compositions as described herein can alter, in various ways, their biophysical properties in aqueous media and on tissues. Therefore, we tested mixtures of synthetic cationic polypeptides and other polymers in vivo.

Example 5

Figure 25:
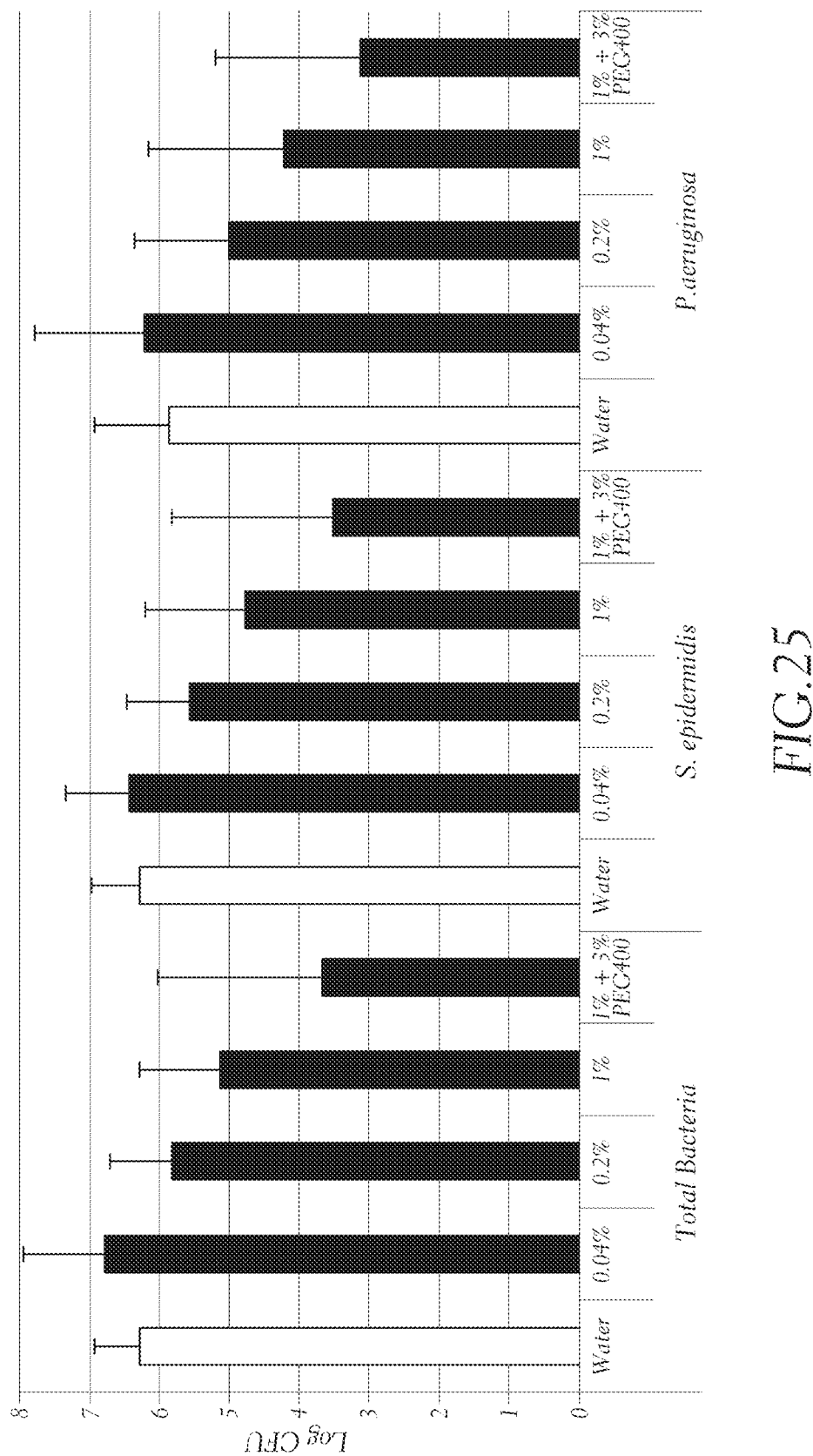
FIG. 25 shows the antimicrobial activity of $K_{100}$(rac-L)$_{20}$ (SEQ ID NO: 12) in an open-wound porcine model. Each wound was contaminated with bacteria (*S. epidermidis, P. aeruginosa* (pig clinical isolate)). After 2 hrs, wounds were rinsed with saline and treated with 5 mL of test article or water. Test articles: $K_{100}$(rac-L)$_{20}$ (SEQ ID NO: 12) at 10, 2, 0.4 mg/mL, 10 mg/mL $K_{100}$(rac-L)$_{20}$ (SEQ ID NO: 12) and 30 mg/mL PEG 400 in water, and deionized water as a control. Gauze soaked in test article or water was placed on top of the wounds. Wounds were biopsied at 4 hrs after treatment.
Figure 26:
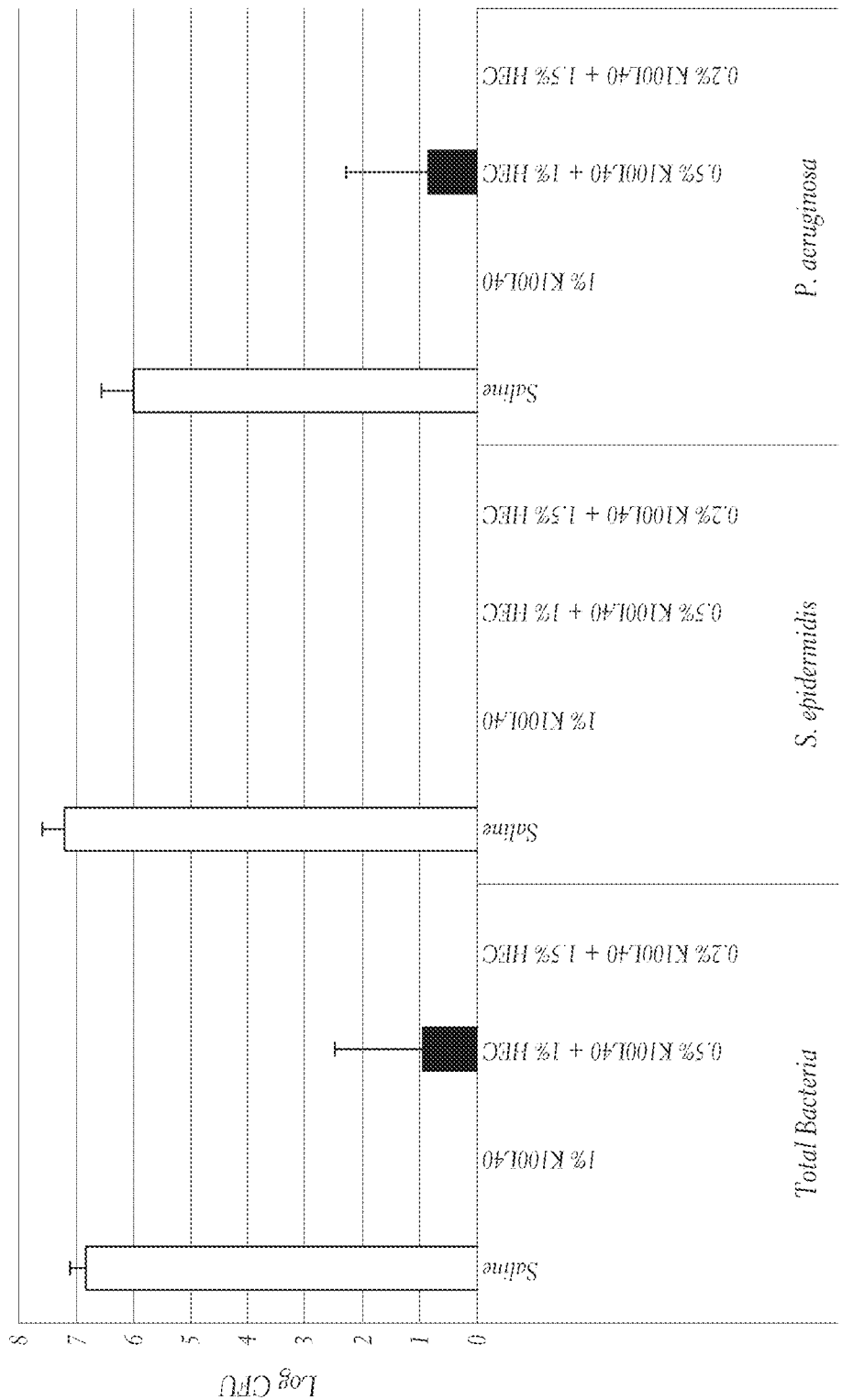
FIG. 26 shows that a $K_{100}L_{40}$ (SEQ ID NO: 19) hydrogel prevents infection in an open-wound porcine model. To each wound hydrogel was applied to the wound bed and to gauze. The hydrogel-soaked gauze was placed on top of wounds. Saline was used as a control. After 15 min. each wound was contaminated with bacteria (*S. epidermidis, P. aeruginosa* (pig clinical isolate)). Hydrogel test articles: $K_{100}L_{40}$ (SEQ ID NO: 19) 10 mg/mL, $K_{100}L_{40}$ (SEQ ID NO: 19) 5 mg/mL and 10 mg/mL HEC, $K_{100}L_{40}$ (SEQ ID NO: 19) 2 mg/mL and 15 mg/mL HEC, and saline as a control. Wounds were biopsied at 4 hrs after hydrogel application.

Aqueous compositions that include mixtures of synthetic cationic polypeptides with two different polymers (polyethylene glycol 400 and hydroxyethyl cellulose) were both found to be effective in vivo. As depicted in FIG. 25, $K_{100}$(rac-L)$_{20}$ (SEQ ID NO: 12) was effective in an porcine open-wound treatment model alone and in combination with PEG 400. As depicted in FIG. 26, $K_{100}L_{40}$ (SEQ ID NO: 19) was effective at preventing microbial contamination alone and in combination with hydroxyethyl cellulose. Further, the data suggests that enhanced biophysical properties of the mixtures can improve antimicrobial activity in vivo over the synthetic cationic copolypeptides alone. The aqueous compositions described herein can be used for any one or more treatments and/or applications, including but not limited to prevention of infections, treatment of infections, treatment for topical anti-infection, treatment for microbial decolonization, wound treatment, surgical site treatment, trauma treatment, burn treatment, treatment of diabetic foot ulcers, eye treatment, treatment of vaginal infections, treatment of urinary tract infections, hand sanitization, for coating prosthetic devices and/or implants, food preservation and solution preservation.

Figure 27:
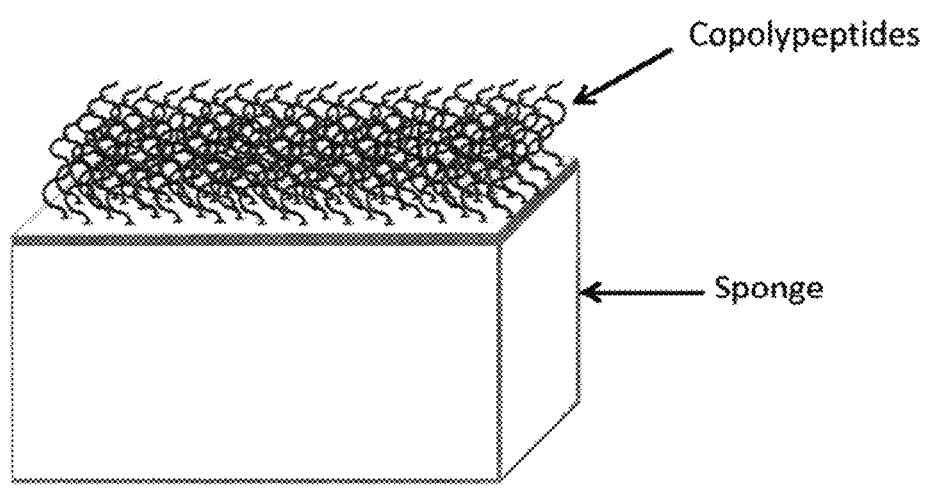
FIG. 27 depicts synthetic cationic polypeptides bound to a medically-acceptable sponge material. This product concept illustrates one way that copolypeptides could be brought into contact with wounds in order to facilitate the delivery of hemostatic and/or antimicrobial activity.
Figure 28:
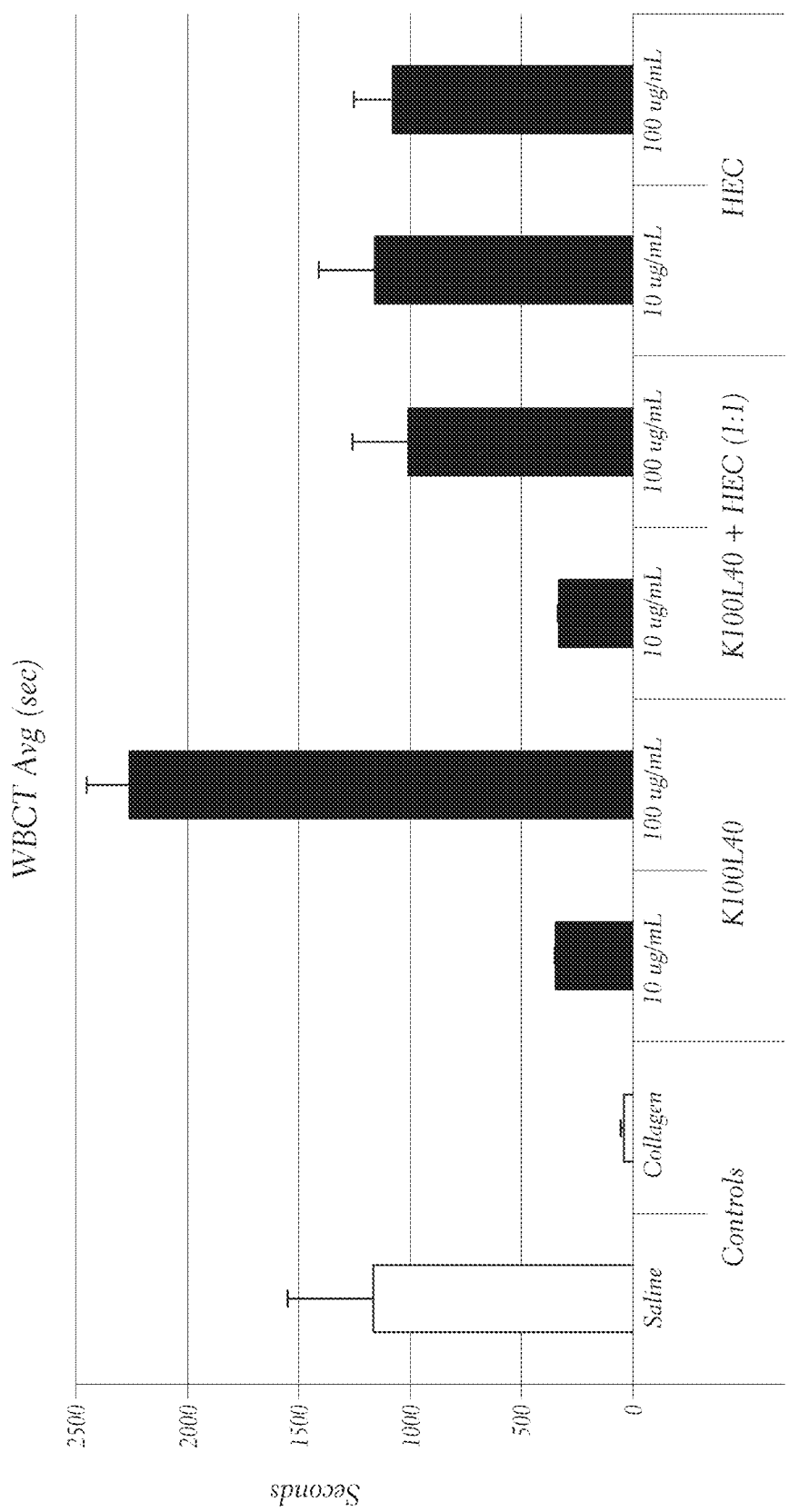
FIG. 28 shows the results of an in vitro whole blood clotting assay with $K_{100}L_{40}$ (SEQ ID NO: 19) and a 1:1 mixture of $K_{100}L_{40}$ (SEQ ID NO: 19) and HEC at 10 and 100 µg/mL. Controls were HEC alone at 10 and 100 µg/mL and a negative control of saline and a positive control of thromboplastin, TF (50 µL in 500 µL of whole blood).
Figure 29:
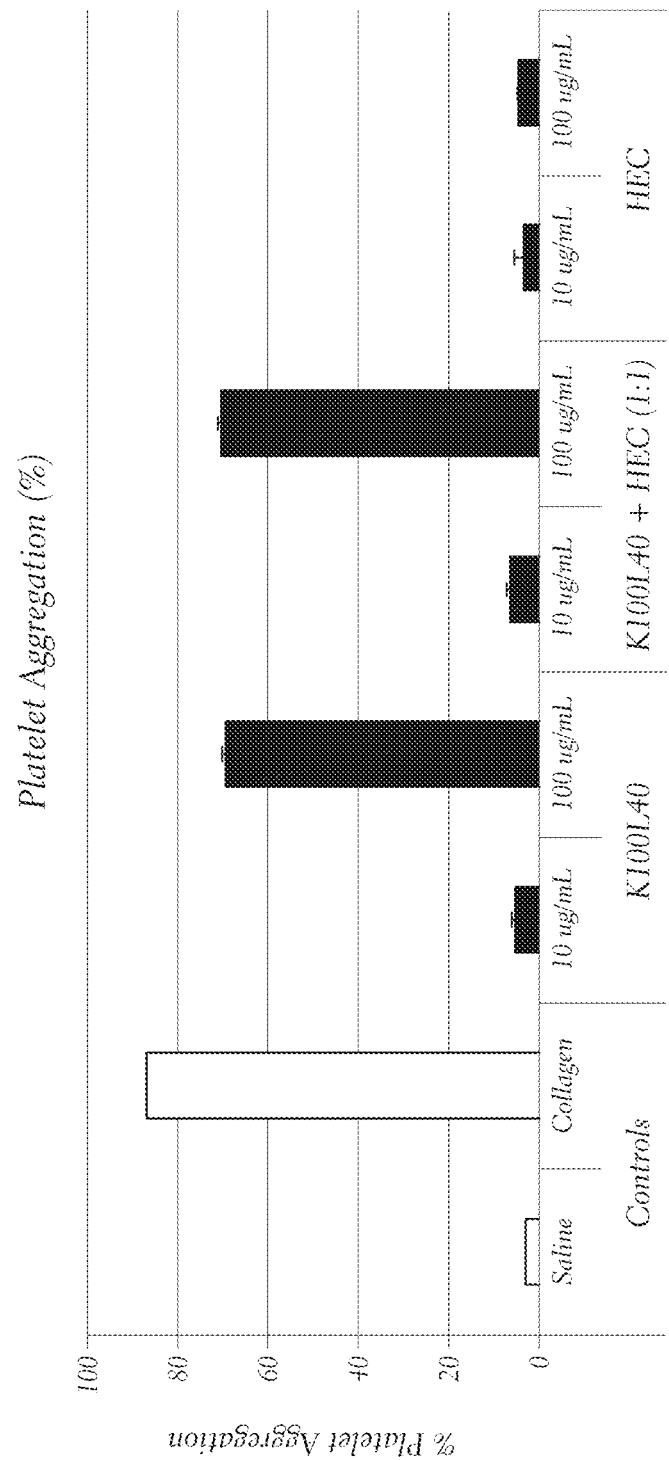
FIG. 29 shows the results of a platelet aggregation assay with $K_{100}L_{40}$ (SEQ ID NO: 19) and a 1:1 mixture of $K_{100}L_{40}$ (SEQ ID NO: 19) and HEC at 10 and 100 µg/mL. Controls were HEC alone at 10 and 100 µg/mL, a negative control of saline, and a positive control of collagen.

The aqueous compositions described herein may be formulated as solutions, emulsions, particles, or hydrogels with a variety of viscoelastic properties to enhance their antimicrobial properties, their barrier properties, or both. In one embodiment, an aqueous composition as described herein comprises a wound wash product with a single lysine-leucine block copolypeptide in water, saline, or other aqueous media that is mixed with a second polymer, typically a surfactant such as poloxamer 407. In one embodiment, an aqueous composition as described herein may comprise a viscous fluid/flowing gel that can be applied through a sprayer to coat various tissues. This could be used in open or laparoscopic approaches. These materials may by themselves or in combination with other materials be formed into a variety of dressings or bandages. These may include constituting or coating a variety of materials such as gauze or sponges. An example would include an aqueous composition as described herein (e.g., containing a synthetic block copolypeptide KxLy) in the form of a coating on gauze or alginate bandages. Another example would include a two-layer material where an aqueous composition as described herein (e.g., containing a synthetic block copolypeptide KxLy alone or with another polymer such as a collagen) coats a face of a relatively inert sponge material (e.g. polyacrylate, polyurethane, or polyhema) (FIG. 27). In this case the embodiment could have the appearance of a rectangular sponge with one coated surface or of a spherical sponge where the entire surface is coated (reminiscent of a tennis ball). This may be particularly advantageous in the treatment of bleeding wounds where hemostasis is required (FIG. 28-29).

An embodiment provides a method for the prevention and/or treatment of infections that includes contacting a tissue of a subject with an aqueous composition as described herein, e.g., to a wound. Another embodiment further includes applying negative-pressure to the treated wound. The subject can be an animal, preferably a human. In an embodiment, the subject is further treated systemically with an antibiotic and/or locally with another antimicrobial, and/or at least one selected from the group consisting of an antibiotic, an anti-biofilm agent, a surfactant, and a combination thereof.

The aqueous compositions described herein can further include one or more of an active pharmaceutical ingredient (API). Examples of such APIs include steroids, pro-inflammatory agents, anti-inflammatory agents, anti-acne agents, preservatives, hemostatic agents, angiogenic agents, wound healing agents, anti-cancer agents and other antimicrobial agents.

What is claimed is:

1. A method of treating a biofilm, comprising:
   selecting a site capable of supporting biofilm formation;
   applying to the site a composition comprising one or more synthetic polypeptide(s) having a length of at least 40 amino acid residues;
   wherein the one or more synthetic polypeptide(s) has a net cationic charge at neutral pH;
   wherein the one or more synthetic polypeptide(s) has at least one cationic segment with a plurality of positively charged amino acid residues and at least one hydrophobic segment with a plurality of hydrophobic amino acid residues; and
   wherein the synthetic cationic polypeptide(s) are configured to self-assemble into multimeric structures in an aqueous composition,
   wherein the one or more synthetic polypeptide(s) inhibits or kills microbes in biofilms.

2. The method of claim 1, wherein the site is selected from the group consisting of an acute wound, a chronic wound, a devitalized tissue, and a foreign body.

3. The method of claim 2, wherein the foreign body is selected from the group consisting of a prosthetic device, mesh, ventilator equipment, and a catheter.

4. The method of claim 3, wherein the mesh is an implantable mesh.

5. The method of claim 3, wherein the mesh is a synthetic mesh.

6. The method of claim 1, wherein the synthetic polypeptide(s) contains one cationic segment and one hydrophobic segment.

7. The method of claim 1, wherein the composition further comprises a pharmaceutically-acceptable polymer that is not a synthetic cationic polypeptide.

8. The method of claim 1, wherein the site comprises a biofilm.

9. The method of claim 1, wherein an antimicrobial activity of the one or more synthetic polypeptide(s) when in an aqueous composition at a concentration of 100 μg/mL or less is greater than 3 logs killing of *Staphylococcus epidermidis* and *Escherichia coli* in standard 60 minute time-kill assays.

10. The method of claim 1, wherein the at least one cationic segment comprises one or more of lysine or arginine.

11. The method of claim 10, wherein the at least one hydrophobic segment comprises one or more of leucine, isoleucine, valine, and alanine.

12. The method of claim 1, wherein the composition further comprises a second pharmaceutically-acceptable polymer that is not a synthetic, cationic polypeptide(s); and
wherein the one or more synthetic polypeptide(s) and the second pharmaceutically-acceptable polymer are mutually miscible in water.

13. The method of claim 12, wherein the amounts of the one or more synthetic polypeptide(s) and the second pharmaceutically-acceptable polymer are each at least about 100 μg/mL based on the total volume of the aqueous composition.

14. The method of claim 13, wherein the amount of the second pharmaceutically-acceptable polymer is at least about 10% by weight, based on the weight of the one or more synthetic polypeptide(s).

15. The method of claim 1, wherein the one or more synthetic polypeptide(s) comprises a block containing 50 to 200 or more lysine amino acid residues.

16. The method of claim 1, wherein the one or more synthetic polypeptide(s) comprises $K_{50}(\text{rac-L})_{10}$ (SEQ ID NO: 1), $K_{50}(\text{rac-L})_{20}$ (SEQ ID NO: 2), $K_{50}(\text{rac-L})_{30}$ (SEQ ID NO: 3), $K_{50}(\text{rac-L})_{40}$ (SEQ ID NO: 4), $K_{50}(\text{rac-L})_{50}$ (SEQ ID NO: 5), $K_{50}L_{10}$ (SEQ ID NO: 6), $K_{50}L_{20}$ (SEQ ID NO: 7), $K_{50}L_{30}$ (SEQ ID NO: 8), $K_{50}L_{40}$ (SEQ ID NO: 9), $K_{50}L_{50}$ (SEQ ID NO: 10), $K_{100}(\text{rac-L})_{10}$ (SEQ ID NO: 11), $K_{100}(\text{rac-L})_{20}$ (SEQ ID NO: 12), $K_{100}(\text{rac-L})_{30}$ (SEQ ID NO: 13), $K_{100}(\text{rac-L})_{40}$ (SEQ ID NO: 14), $K_{100}(\text{rac-L})_{50}$ (SEQ ID NO: 15), $K_{100}L_{10}$ (SEQ ID NO: 16), $K_{100}L_{20}$ (SEQ ID NO: 17), $K_{100}L_{30}$ (SEQ ID NO: 18), $K_{100}L_{40}$ (SEQ ID NO: 19), $K_{100}L_{50}$ (SEQ ID NO: 20), $K_{200}(\text{rac-L})_{10}$ (SEQ ID NO: 21), $K_{200}(\text{rac-L})_{20}$ (SEQ ID NO: 22), $K_{200}(\text{rac-L})_{30}$ (SEQ ID NO: 23), $K_{200}(\text{rac-L})_{40}$ (SEQ ID NO: 24), $K_{200}(\text{rac-L})_{50}$ (SEQ ID NO: 25), $K_{200}L_{10}$ (SEQ ID NO: 26), $K_{200}L_{20}$ (SEQ ID NO: 27), $K_{200}L_{30}$ (SEQ ID NO: 28), $K_{20}L_{40}$ (SEQ ID NO: 29), $K_{200}L_{50}$ (SEQ ID NO: 30), or combinations of more than one of the foregoing.

17. The method of claim 1, wherein the composition is characterized by a barrier activity, as measured by a decrease in the diffusion rate of an anionic dye.

* * * * *

SEQUENCE LISTING

```
<160> NUMBER OF SEQ ID NOS: 32

<210> SEQ ID NO 1
<211> LENGTH: 60
<212> TYPE: PRT
<213> ORGANISM: Artificial Sequence
<220> FEATURE:
<223> OTHER INFORMATION: K50(rac-L)10
<220> FEATURE:
<221> NAME/KEY: rac-L
<222> LOCATION: (51)..(60)

<400> SEQUENCE: 1

Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys
                20                  25                  30

Lys Lys Lys Lys Lys Lys Lys Lys Lys Lys Lys Lys Lys Lys Lys
            35                  40                  45

Lys Lys Leu Leu Leu Leu Leu Leu Leu Leu Leu Leu
        50                  55                  60

<210> SEQ ID NO 2
<211> LENGTH: 70
<212> TYPE: PRT
<213> ORGANISM: Artificial Sequence
<220> FEATURE:
<223> OTHER INFORMATION: K50(rac-L)20
<220> FEATURE:
<221> NAME/KEY: rac-L
<222> LOCATION: (51)..(70)

<400> SEQUENCE: 2

Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys
                20                  25                  30

Lys Lys Lys Lys Lys Lys Lys Lys Lys Lys Lys Lys Lys Lys Lys
            35                  40                  45

Lys Lys Leu Leu Leu Leu Leu Leu Leu Leu Leu Leu Leu Leu Leu
        50                  55                  60
```

```
Leu Leu Leu Leu Leu Leu
 65                  70

<210> SEQ ID NO 3
<211> LENGTH: 80
<212> TYPE: PRT
<213> ORGANISM: Artificial Sequence
<220> FEATURE:
<223> OTHER INFORMATION: K50(rac-L)30
<220> FEATURE:
<221> NAME/KEY: rac-L
<222> LOCATION: (51)..(80)

<400> SEQUENCE: 3

Lys Lys Lys Lys Lys Lys Lys Lys Lys Lys Lys Lys Lys Lys Lys Lys
 1               5                  10                  15

Lys Lys Lys Lys Lys Lys Lys Lys Lys Lys Lys Lys Lys Lys
             20                  25                  30

Lys Lys Lys Lys Lys Lys Lys Lys Lys Lys Lys Lys Lys Lys
         35                  40                  45

Lys Lys Leu Leu Leu Leu Leu Leu Leu Leu Leu Leu Leu Leu
     50                  55                  60

Leu Leu Leu Leu Leu Leu Leu Leu Leu Leu Leu Leu Leu Leu Leu Leu
 65                  70                  75                  80

<210> SEQ ID NO 4
<211> LENGTH: 90
<212> TYPE: PRT
<213> ORGANISM: Artificial Sequence
<220> FEATURE:
<223> OTHER INFORMATION: K50(rac-L)40
<220> FEATURE:
<221> NAME/KEY: rac-L
<222> LOCATION: (51)..(90)

<400> SEQUENCE: 4

Lys Lys Lys Lys Lys Lys Lys Lys Lys Lys Lys Lys Lys Lys Lys Lys
 1               5                  10                  15

Lys Lys Lys Lys Lys Lys Lys Lys Lys Lys Lys Lys Lys Lys
             20                  25                  30

Lys Lys Lys Lys Lys Lys Lys Lys Lys Lys Lys Lys Lys Lys
         35                  40                  45

Lys Lys Leu Leu Leu Leu Leu Leu Leu Leu Leu Leu Leu Leu
     50                  55                  60

Leu Leu Leu Leu Leu Leu Leu Leu Leu Leu Leu Leu Leu Leu Leu Leu
 65                  70                  75                  80

Leu Leu Leu Leu Leu Leu Leu Leu Leu Leu
                 85                  90

<210> SEQ ID NO 5
<211> LENGTH: 100
<212> TYPE: PRT
<213> ORGANISM: Artificial Sequence
<220> FEATURE:
<223> OTHER INFORMATION: K50(rac-L)50
<220> FEATURE:
<221> NAME/KEY: rac-L
<222> LOCATION: (51)..(100)

<400> SEQUENCE: 5

Lys Lys Lys Lys Lys Lys Lys Lys Lys Lys Lys Lys Lys Lys Lys Lys
 1               5                  10                  15
```

Lys Lys Lys Lys Lys Lys Lys Lys Lys Lys Lys Lys
        20                  25                  30

Lys Lys Lys Lys Lys Lys Lys Lys Lys Lys Lys Lys
        35                  40                  45

Lys Lys Leu Leu Leu Leu Leu Leu Leu Leu Leu Leu Leu Leu
    50                  55                  60

Leu Leu Leu Leu Leu Leu Leu Leu Leu Leu Leu Leu Leu Leu Leu Leu
65                  70                  75                  80

Leu Leu Leu Leu Leu Leu Leu Leu Leu Leu Leu Leu Leu Leu Leu
                85                  90                  95

Leu Leu Leu Leu
        100

<210> SEQ ID NO 6
<211> LENGTH: 60
<212> TYPE: PRT
<213> ORGANISM: Artificial Sequence
<220> FEATURE:
<223> OTHER INFORMATION: K50L10

<400> SEQUENCE: 6

Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys
            20                  25                  30

Lys Lys Lys Lys Lys Lys Lys Lys Lys Lys Lys Lys Lys Lys Lys
            35                  40                  45

Lys Lys Leu Leu Leu Leu Leu Leu Leu Leu Leu Leu
        50                  55                  60

<210> SEQ ID NO 7
<211> LENGTH: 70
<212> TYPE: PRT
<213> ORGANISM: Artificial Sequence
<220> FEATURE:
<223> OTHER INFORMATION: K50L20

<400> SEQUENCE: 7

Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys
            20                  25                  30

Lys Lys Lys Lys Lys Lys Lys Lys Lys Lys Lys Lys Lys Lys Lys
            35                  40                  45

Lys Lys Leu Leu Leu Leu Leu Leu Leu Leu Leu Leu Leu Leu Leu
        50                  55                  60

Leu Leu Leu Leu Leu Leu
65                  70

<210> SEQ ID NO 8
<211> LENGTH: 80
<212> TYPE: PRT
<213> ORGANISM: Artificial Sequence
<220> FEATURE:
<223> OTHER INFORMATION: K50L30

<400> SEQUENCE: 8

Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys

```
              20                  25                  30

Lys Lys Lys Lys Lys Lys Lys Lys Lys Lys Lys Lys Lys Lys
                35                  40                  45

Lys Lys Leu Leu Leu Leu Leu Leu Leu Leu Leu Leu Leu Leu
 50                  55                  60

Leu Leu Leu Leu Leu Leu Leu Leu Leu Leu Leu Leu Leu Leu
 65                  70                  75                  80
```

```
<210> SEQ ID NO 9
<211> LENGTH: 90
<212> TYPE: PRT
<213> ORGANISM: Artificial Sequence
<220> FEATURE:
<223> OTHER INFORMATION: K50L40

<400> SEQUENCE: 9

Lys Lys Lys Lys Lys Lys Lys Lys Lys Lys Lys Lys Lys Lys Lys Lys
 1               5                  10                  15

Lys Lys Lys Lys Lys Lys Lys Lys Lys Lys Lys Lys Lys Lys
                20                  25                  30

Lys Lys Lys Lys Lys Lys Lys Lys Lys Lys Lys Lys Lys Lys
                35                  40                  45

Lys Lys Leu Leu Leu Leu Leu Leu Leu Leu Leu Leu Leu Leu
 50                  55                  60

Leu Leu Leu Leu Leu Leu Leu Leu Leu Leu Leu Leu Leu Leu
 65                  70                  75                  80

Leu Leu Leu Leu Leu Leu Leu Leu Leu Leu
                85                  90
```

```
<210> SEQ ID NO 10
<211> LENGTH: 100
<212> TYPE: PRT
<213> ORGANISM: Artificial Sequence
<220> FEATURE:
<223> OTHER INFORMATION: K50L50

<400> SEQUENCE: 10

Lys Lys Lys Lys Lys Lys Lys Lys Lys Lys Lys Lys Lys Lys Lys Lys
 1               5                  10                  15

Lys Lys Lys Lys Lys Lys Lys Lys Lys Lys Lys Lys Lys Lys
                20                  25                  30

Lys Lys Lys Lys Lys Lys Lys Lys Lys Lys Lys Lys Lys Lys
                35                  40                  45

Lys Lys Leu Leu Leu Leu Leu Leu Leu Leu Leu Leu Leu Leu
 50                  55                  60

Leu Leu Leu Leu Leu Leu Leu Leu Leu Leu Leu Leu Leu Leu
 65                  70                  75                  80

Leu Leu Leu Leu Leu Leu Leu Leu Leu Leu Leu Leu Leu Leu
                85                  90                  95

Leu Leu Leu Leu
                100
```

```
<210> SEQ ID NO 11
<211> LENGTH: 110
<212> TYPE: PRT
<213> ORGANISM: Artificial Sequence
<220> FEATURE:
<223> OTHER INFORMATION: K100(rac-L)10
<220> FEATURE:
<221> NAME/KEY: rac-L
```

<222> LOCATION: (101)..(110)

<400> SEQUENCE: 11

Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys
            20                  25                  30

Lys Lys Lys Lys Lys Lys Lys Lys Lys Lys Lys Lys Lys Lys Lys
        35                  40                  45

Lys Lys Lys Lys Lys Lys Lys Lys Lys Lys Lys Lys Lys Lys Lys
    50                  55                  60

Lys Lys Lys Lys Lys Lys Lys Lys Lys Lys Lys Lys Lys Lys Lys
65              70                  75                  80

Lys Lys Lys Lys Lys Lys Lys Lys Lys Lys Lys Lys Lys Lys Lys
            85                  90                  95

Lys Lys Lys Lys Leu Leu Leu Leu Leu Leu Leu Leu Leu Leu
        100                 105                 110

<210> SEQ ID NO 12
<211> LENGTH: 120
<212> TYPE: PRT
<213> ORGANISM: Artificial Sequence
<220> FEATURE:
<223> OTHER INFORMATION: K100(rac-L)20
<220> FEATURE:
<221> NAME/KEY: rac-L
<222> LOCATION: (101)..(120)

<400> SEQUENCE: 12

Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys
            20                  25                  30

Lys Lys Lys Lys Lys Lys Lys Lys Lys Lys Lys Lys Lys Lys Lys
        35                  40                  45

Lys Lys Lys Lys Lys Lys Lys Lys Lys Lys Lys Lys Lys Lys Lys
    50                  55                  60

Lys Lys Lys Lys Lys Lys Lys Lys Lys Lys Lys Lys Lys Lys Lys
65              70                  75                  80

Lys Lys Lys Lys Lys Lys Lys Lys Lys Lys Lys Lys Lys Lys Lys
            85                  90                  95

Lys Lys Lys Lys Leu Leu Leu Leu Leu Leu Leu Leu Leu Leu Leu Leu
        100                 105                 110

Leu Leu Leu Leu Leu Leu Leu Leu
        115                 120

<210> SEQ ID NO 13
<211> LENGTH: 130
<212> TYPE: PRT
<213> ORGANISM: Artificial Sequence
<220> FEATURE:
<223> OTHER INFORMATION: K100(rac-L)30
<220> FEATURE:
<221> NAME/KEY: rac-L
<222> LOCATION: (101)..(130)

<400> SEQUENCE: 13

Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys

```
                    20                  25                  30

Lys Lys Lys Lys Lys Lys Lys Lys Lys Lys Lys Lys Lys Lys Lys
            35                  40                  45

Lys Lys Lys Lys Lys Lys Lys Lys Lys Lys Lys Lys Lys Lys Lys
        50                  55                  60

Lys Lys Lys Lys Lys Lys Lys Lys Lys Lys Lys Lys Lys Lys Lys
65                  70                  75                  80

Lys Lys Lys Lys Lys Lys Lys Lys Lys Lys Lys Lys Lys Lys Lys
                85                  90                  95

Lys Lys Lys Lys Leu Leu Leu Leu Leu Leu Leu Leu Leu Leu Leu
            100                 105                 110

Leu Leu Leu Leu Leu Leu Leu Leu Leu Leu Leu Leu Leu Leu Leu
        115                 120                 125

Leu Leu
    130

<210> SEQ ID NO 14
<211> LENGTH: 140
<212> TYPE: PRT
<213> ORGANISM: Artificial Sequence
<220> FEATURE:
<223> OTHER INFORMATION: K100(rac-L)40
<220> FEATURE:
<221> NAME/KEY: rac-L
<222> LOCATION: (101)..(140)

<400> SEQUENCE: 14

Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys
            20                  25                  30

Lys Lys Lys Lys Lys Lys Lys Lys Lys Lys Lys Lys Lys Lys Lys
        35                  40                  45

Lys Lys Lys Lys Lys Lys Lys Lys Lys Lys Lys Lys Lys Lys Lys
    50                  55                  60

Lys Lys Lys Lys Lys Lys Lys Lys Lys Lys Lys Lys Lys Lys Lys
65                  70                  75                  80

Lys Lys Lys Lys Lys Lys Lys Lys Lys Lys Lys Lys Lys Lys Lys
                85                  90                  95

Lys Lys Lys Lys Leu Leu Leu Leu Leu Leu Leu Leu Leu Leu Leu
            100                 105                 110

Leu Leu Leu Leu Leu Leu Leu Leu Leu Leu Leu Leu Leu Leu Leu
        115                 120                 125

Leu Leu Leu Leu Leu Leu Leu Leu Leu Leu
    130                 135                 140

<210> SEQ ID NO 15
<211> LENGTH: 150
<212> TYPE: PRT
<213> ORGANISM: Artificial Sequence
<220> FEATURE:
<223> OTHER INFORMATION: K100(rac-L)50
<220> FEATURE:
<221> NAME/KEY: rac-L
<222> LOCATION: (101)..(150)

<400> SEQUENCE: 15

Lys Lys Lys Lys Lys Lys Lys Lys Lys Lys Lys Lys Lys Lys Lys
1               5                   10                  15
```

```
Lys Lys Lys Lys Lys Lys Lys Lys Lys Lys Lys Lys
            20                  25                  30

Lys Lys Lys Lys Lys Lys Lys Lys Lys Lys Lys Lys
            35                  40                  45

Lys Lys Lys Lys Lys Lys Lys Lys Lys Lys Lys Lys
            50                  55                  60

Lys Lys Lys Lys Lys Lys Lys Lys Lys Lys Lys Lys
65                  70                  75                  80

Lys Lys Lys Lys Lys Lys Lys Lys Lys Lys Lys Lys
            85                  90                  95

Lys Lys Lys Lys Leu Leu Leu Leu Leu Leu Leu Leu Leu Leu Leu
            100                 105                 110

Leu Leu Leu Leu Leu Leu Leu Leu Leu Leu Leu Leu Leu Leu Leu
            115                 120                 125

Leu Leu Leu Leu Leu Leu Leu Leu Leu Leu Leu Leu Leu Leu Leu
            130                 135                 140

Leu Leu Leu Leu Leu Leu
145                 150

<210> SEQ ID NO 16
<211> LENGTH: 110
<212> TYPE: PRT
<213> ORGANISM: Artificial Sequence
<220> FEATURE:
<223> OTHER INFORMATION: K100L10

<400> SEQUENCE: 16

Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys
            20                  25                  30

Lys Lys Lys Lys Lys Lys Lys Lys Lys Lys Lys Lys
            35                  40                  45

Lys Lys Lys Lys Lys Lys Lys Lys Lys Lys Lys Lys
            50                  55                  60

Lys Lys Lys Lys Lys Lys Lys Lys Lys Lys Lys Lys
65                  70                  75                  80

Lys Lys Lys Lys Lys Lys Lys Lys Lys Lys Lys Lys
            85                  90                  95

Lys Lys Lys Lys Leu Leu Leu Leu Leu Leu Leu Leu Leu
            100                 105                 110

<210> SEQ ID NO 17
<211> LENGTH: 120
<212> TYPE: PRT
<213> ORGANISM: Artificial Sequence
<220> FEATURE:
<223> OTHER INFORMATION: K100L20

<400> SEQUENCE: 17

Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys
            20                  25                  30

Lys Lys Lys Lys Lys Lys Lys Lys Lys Lys Lys Lys
            35                  40                  45

Lys Lys Lys Lys Lys Lys Lys Lys Lys Lys Lys Lys Lys Lys
            50                  55                  60
```

```
Lys Lys Lys Lys Lys Lys Lys Lys Lys Lys Lys Lys Lys Lys Lys Lys
 65                  70                  75                  80

Lys Lys Lys Lys Lys Lys Lys Lys Lys Lys Lys Lys Lys Lys Lys
                 85                  90                  95

Lys Lys Lys Lys Leu Leu Leu Leu Leu Leu Leu Leu Leu Leu Leu
             100                 105                 110

Leu Leu Leu Leu Leu Leu Leu Leu
         115                 120

<210> SEQ ID NO 18
<211> LENGTH: 130
<212> TYPE: PRT
<213> ORGANISM: Artificial Sequence
<220> FEATURE:
<223> OTHER INFORMATION: K100L30

<400> SEQUENCE: 18

Lys Lys Lys Lys Lys Lys Lys Lys Lys Lys Lys Lys Lys Lys Lys Lys
 1               5                  10                  15

Lys Lys Lys Lys Lys Lys Lys Lys Lys Lys Lys Lys Lys Lys Lys
             20                  25                  30

Lys Lys Lys Lys Lys Lys Lys Lys Lys Lys Lys Lys Lys Lys Lys
         35                  40                  45

Lys Lys Lys Lys Lys Lys Lys Lys Lys Lys Lys Lys Lys Lys Lys
     50                  55                  60

Lys Lys Lys Lys Lys Lys Lys Lys Lys Lys Lys Lys Lys Lys Lys Lys
 65                  70                  75                  80

Lys Lys Lys Lys Lys Lys Lys Lys Lys Lys Lys Lys Lys Lys Lys
                 85                  90                  95

Lys Lys Lys Lys Leu Leu Leu Leu Leu Leu Leu Leu Leu Leu Leu
             100                 105                 110

Leu Leu Leu Leu Leu Leu Leu Leu Leu Leu Leu Leu Leu Leu Leu
         115                 120                 125

Leu Leu
    130

<210> SEQ ID NO 19
<211> LENGTH: 140
<212> TYPE: PRT
<213> ORGANISM: Artificial Sequence
<220> FEATURE:
<223> OTHER INFORMATION: K100L40

<400> SEQUENCE: 19

Lys Lys Lys Lys Lys Lys Lys Lys Lys Lys Lys Lys Lys Lys Lys Lys
 1               5                  10                  15

Lys Lys Lys Lys Lys Lys Lys Lys Lys Lys Lys Lys Lys Lys Lys
             20                  25                  30

Lys Lys Lys Lys Lys Lys Lys Lys Lys Lys Lys Lys Lys Lys Lys
         35                  40                  45

Lys Lys Lys Lys Lys Lys Lys Lys Lys Lys Lys Lys Lys Lys Lys
     50                  55                  60

Lys Lys Lys Lys Lys Lys Lys Lys Lys Lys Lys Lys Lys Lys Lys Lys
 65                  70                  75                  80

Lys Lys Lys Lys Lys Lys Lys Lys Lys Lys Lys Lys Lys Lys Lys
                 85                  90                  95

Lys Lys Lys Lys Leu Leu Leu Leu Leu Leu Leu Leu Leu Leu Leu Leu
```

```
                    100                 105                 110

Leu Leu Leu Leu Leu Leu Leu Leu Leu Leu Leu Leu Leu Leu Leu
        115                 120                 125

Leu Leu Leu Leu Leu Leu Leu Leu Leu Leu Leu
        130                 135             140

<210> SEQ ID NO 20
<211> LENGTH: 150
<212> TYPE: PRT
<213> ORGANISM: Artificial Sequence
<220> FEATURE:
<223> OTHER INFORMATION: K100L50

<400> SEQUENCE: 20

Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys
            20                  25                  30

Lys Lys Lys Lys Lys Lys Lys Lys Lys Lys Lys Lys Lys Lys Lys
        35                  40                  45

Lys Lys Lys Lys Lys Lys Lys Lys Lys Lys Lys Lys Lys Lys Lys
50                  55                  60

Lys Lys Lys Lys Lys Lys Lys Lys Lys Lys Lys Lys Lys Lys Lys
65                  70                  75                  80

Lys Lys Lys Lys Lys Lys Lys Lys Lys Lys Lys Lys Lys Lys Lys
                85                  90                  95

Lys Lys Lys Lys Leu Leu Leu Leu Leu Leu Leu Leu Leu Leu Leu
            100                 105                 110

Leu Leu Leu Leu Leu Leu Leu Leu Leu Leu Leu Leu Leu Leu Leu
        115                 120                 125

Leu Leu Leu Leu Leu Leu Leu Leu Leu Leu Leu Leu Leu Leu Leu
    130                 135                 140

Leu Leu Leu Leu Leu Leu
145                 150

<210> SEQ ID NO 21
<211> LENGTH: 210
<212> TYPE: PRT
<213> ORGANISM: Artificial Sequence
<220> FEATURE:
<223> OTHER INFORMATION: K200(rac-L)10
<220> FEATURE:
<221> NAME/KEY: rac-L
<222> LOCATION: (201)..(210)

<400> SEQUENCE: 21

Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys
            20                  25                  30

Lys Lys Lys Lys Lys Lys Lys Lys Lys Lys Lys Lys Lys Lys Lys
        35                  40                  45

Lys Lys Lys Lys Lys Lys Lys Lys Lys Lys Lys Lys Lys Lys Lys
    50                  55                  60

Lys Lys Lys Lys Lys Lys Lys Lys Lys Lys Lys Lys Lys Lys Lys
65                  70                  75                  80

Lys Lys Lys Lys Lys Lys Lys Lys Lys Lys Lys Lys Lys Lys Lys
                85                  90                  95
```

Lys Lys Lys Lys Lys Lys Lys Lys Lys Lys Lys Lys Lys Lys
            100                 105                 110

Lys Lys Lys Lys Lys Lys Lys Lys Lys Lys Lys Lys Lys Lys
        115                 120                 125

Lys Lys Lys Lys Lys Lys Lys Lys Lys Lys Lys Lys Lys Lys
    130                 135                 140

Lys Lys Lys Lys Lys Lys Lys Lys Lys Lys Lys Lys Lys Lys
145                 150                 155                 160

Lys Lys Lys Lys Lys Lys Lys Lys Lys Lys Lys Lys Lys Lys
                165                 170                 175

Lys Lys Lys Lys Lys Lys Lys Lys Lys Lys Lys Lys Lys Lys
            180                 185                 190

Lys Lys Lys Lys Lys Lys Lys Lys Leu Leu Leu Leu Leu Leu
        195                 200                 205

Leu Leu
    210

<210> SEQ ID NO 22
<211> LENGTH: 220
<212> TYPE: PRT
<213> ORGANISM: Artificial Sequence
<220> FEATURE:
<223> OTHER INFORMATION: K200(rac-L)20
<220> FEATURE:
<221> NAME/KEY: rac-L
<222> LOCATION: (201)..(220)

<400> SEQUENCE: 22

Lys Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys
        20                  25                  30

Lys Lys Lys Lys Lys Lys Lys Lys Lys Lys Lys Lys Lys Lys
    35                  40                  45

Lys Lys Lys Lys Lys Lys Lys Lys Lys Lys Lys Lys Lys Lys
50                  55                  60

Lys Lys Lys Lys Lys Lys Lys Lys Lys Lys Lys Lys Lys Lys Lys Lys
65                  70                  75                  80

Lys Lys Lys Lys Lys Lys Lys Lys Lys Lys Lys Lys Lys Lys
                85                  90                  95

Lys Lys Lys Lys Lys Lys Lys Lys Lys Lys Lys Lys Lys Lys
            100                 105                 110

Lys Lys Lys Lys Lys Lys Lys Lys Lys Lys Lys Lys Lys Lys
        115                 120                 125

Lys Lys Lys Lys Lys Lys Lys Lys Lys Lys Lys Lys Lys Lys
    130                 135                 140

Lys Lys Lys Lys Lys Lys Lys Lys Lys Lys Lys Lys Lys Lys
145                 150                 155                 160

Lys Lys Lys Lys Lys Lys Lys Lys Lys Lys Lys Lys Lys Lys
                165                 170                 175

Lys Lys Lys Lys Lys Lys Lys Lys Lys Lys Lys Lys Lys Lys
            180                 185                 190

Lys Lys Lys Lys Lys Lys Lys Lys Leu Leu Leu Leu Leu Leu
        195                 200                 205

Leu Leu Leu Leu Leu Leu Leu Leu Leu Leu Leu Leu
    210                 215                 220

```
<210> SEQ ID NO 23
<211> LENGTH: 230
<212> TYPE: PRT
<213> ORGANISM: Artificial Sequence
<220> FEATURE:
<223> OTHER INFORMATION: K200(rac-L)30
<220> FEATURE:
<221> NAME/KEY: rac-L
<222> LOCATION: (201)..(230)

<400> SEQUENCE: 23

Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys
            20                  25                  30

Lys Lys Lys Lys Lys Lys Lys Lys Lys Lys Lys Lys Lys Lys Lys
        35                  40                  45

Lys Lys Lys Lys Lys Lys Lys Lys Lys Lys Lys Lys Lys Lys Lys
    50                  55                  60

Lys Lys Lys Lys Lys Lys Lys Lys Lys Lys Lys Lys Lys Lys Lys
65                  70                  75                  80

Lys Lys Lys Lys Lys Lys Lys Lys Lys Lys Lys Lys Lys Lys Lys
                85                  90                  95

Lys Lys Lys Lys Lys Lys Lys Lys Lys Lys Lys Lys Lys Lys Lys
            100                 105                 110

Lys Lys Lys Lys Lys Lys Lys Lys Lys Lys Lys Lys Lys Lys Lys
        115                 120                 125

Lys Lys Lys Lys Lys Lys Lys Lys Lys Lys Lys Lys Lys Lys Lys
    130                 135                 140

Lys Lys Lys Lys Lys Lys Lys Lys Lys Lys Lys Lys Lys Lys Lys
145                 150                 155                 160

Lys Lys Lys Lys Lys Lys Lys Lys Lys Lys Lys Lys Lys Lys Lys
                165                 170                 175

Lys Lys Lys Lys Lys Lys Lys Lys Lys Lys Lys Lys Lys Lys Lys
            180                 185                 190

Lys Lys Lys Lys Lys Lys Lys Leu Leu Leu Leu Leu Leu Leu Leu
        195                 200                 205

Leu Leu Leu Leu Leu Leu Leu Leu Leu Leu Leu Leu Leu Leu Leu
    210                 215                 220

Leu Leu Leu Leu Leu Leu
225                 230

<210> SEQ ID NO 24
<211> LENGTH: 240
<212> TYPE: PRT
<213> ORGANISM: Artificial Sequence
<220> FEATURE:
<223> OTHER INFORMATION: K200(rac-L)40
<220> FEATURE:
<221> NAME/KEY: rac-L
<222> LOCATION: (201)..(240)

<400> SEQUENCE: 24

Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys
            20                  25                  30

Lys Lys Lys Lys Lys Lys Lys Lys Lys Lys Lys Lys Lys Lys Lys
        35                  40                  45
```

```
Lys Lys Lys Lys Lys Lys Lys Lys Lys Lys Lys Lys Lys Lys Lys Lys
 50                  55                  60
Lys Lys Lys Lys Lys Lys Lys Lys Lys Lys Lys Lys Lys Lys Lys Lys
 65                  70                  75                  80
Lys Lys Lys Lys Lys Lys Lys Lys Lys Lys Lys Lys Lys Lys Lys Lys
             85                  90                  95
Lys Lys Lys Lys Lys Lys Lys Lys Lys Lys Lys Lys Lys Lys Lys Lys
            100                 105                 110
Lys Lys Lys Lys Lys Lys Lys Lys Lys Lys Lys Lys Lys Lys Lys Lys
        115                 120                 125
Lys Lys Lys Lys Lys Lys Lys Lys Lys Lys Lys Lys Lys Lys Lys Lys
        130                 135                 140
Lys Lys Lys Lys Lys Lys Lys Lys Lys Lys Lys Lys Lys Lys Lys Lys
145                 150                 155                 160
Lys Lys Lys Lys Lys Lys Lys Lys Lys Lys Lys Lys Lys Lys Lys Lys
            165                 170                 175
Lys Lys Lys Lys Lys Lys Lys Lys Lys Lys Lys Lys Lys Lys Lys Lys
            180                 185                 190
Lys Lys Lys Lys Lys Lys Lys Lys Leu Leu Leu Leu Leu Leu Leu Leu
        195                 200                 205
Leu Leu Leu Leu Leu Leu Leu Leu Leu Leu Leu Leu Leu Leu Leu Leu
        210                 215                 220
Leu Leu Leu Leu Leu Leu Leu Leu Leu Leu Leu Leu Leu Leu Leu Leu
225                 230                 235                 240

<210> SEQ ID NO 25
<211> LENGTH: 250
<212> TYPE: PRT
<213> ORGANISM: Artificial Sequence
<220> FEATURE:
<223> OTHER INFORMATION: K200(rac-L)50
<220> FEATURE:
<221> NAME/KEY: rac-L
<222> LOCATION: (201)..(250)

<400> SEQUENCE: 25

Lys Lys Lys Lys Lys Lys Lys Lys Lys Lys Lys Lys Lys Lys Lys Lys
 1                   5                  10                  15
Lys Lys Lys Lys Lys Lys Lys Lys Lys Lys Lys Lys Lys Lys Lys Lys
             20                  25                  30
Lys Lys Lys Lys Lys Lys Lys Lys Lys Lys Lys Lys Lys Lys Lys Lys
         35                  40                  45
Lys Lys Lys Lys Lys Lys Lys Lys Lys Lys Lys Lys Lys Lys Lys Lys
 50                  55                  60
Lys Lys Lys Lys Lys Lys Lys Lys Lys Lys Lys Lys Lys Lys Lys Lys
 65                  70                  75                  80
Lys Lys Lys Lys Lys Lys Lys Lys Lys Lys Lys Lys Lys Lys Lys Lys
             85                  90                  95
Lys Lys Lys Lys Lys Lys Lys Lys Lys Lys Lys Lys Lys Lys Lys Lys
            100                 105                 110
Lys Lys Lys Lys Lys Lys Lys Lys Lys Lys Lys Lys Lys Lys Lys Lys
        115                 120                 125
Lys Lys Lys Lys Lys Lys Lys Lys Lys Lys Lys Lys Lys Lys Lys Lys
        130                 135                 140
Lys Lys Lys Lys Lys Lys Lys Lys Lys Lys Lys Lys Lys Lys Lys Lys
145                 150                 155                 160
```

Lys Lys Lys Lys Lys Lys Lys Lys Lys Lys Lys Lys Lys Lys
            165                 170                 175

Lys Lys Lys Lys Lys Lys Lys Lys Lys Lys Lys Lys Lys Lys
        180                 185                 190

Lys Lys Lys Lys Lys Lys Lys Leu Leu Leu Leu Leu Leu Leu
    195                 200                 205

Leu Leu Leu Leu Leu Leu Leu Leu Leu Leu Leu Leu Leu Leu
210                 215                 220

Leu Leu Leu Leu Leu Leu Leu Leu Leu Leu Leu Leu Leu Leu
225                 230                 235                 240

Leu Leu Leu Leu Leu Leu Leu Leu Leu Leu
            245                 250

<210> SEQ ID NO 26
<211> LENGTH: 210
<212> TYPE: PRT
<213> ORGANISM: Artificial Sequence
<220> FEATURE:
<223> OTHER INFORMATION: K200L10

<400> SEQUENCE: 26

Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys
            20                  25                  30

Lys Lys Lys Lys Lys Lys Lys Lys Lys Lys Lys Lys Lys Lys Lys
        35                  40                  45

Lys Lys Lys Lys Lys Lys Lys Lys Lys Lys Lys Lys Lys Lys Lys
    50                  55                  60

Lys Lys Lys Lys Lys Lys Lys Lys Lys Lys Lys Lys Lys Lys Lys
65                  70                  75                  80

Lys Lys Lys Lys Lys Lys Lys Lys Lys Lys Lys Lys Lys Lys Lys
            85                  90                  95

Lys Lys Lys Lys Lys Lys Lys Lys Lys Lys Lys Lys Lys Lys Lys
        100                 105                 110

Lys Lys Lys Lys Lys Lys Lys Lys Lys Lys Lys Lys Lys Lys Lys
    115                 120                 125

Lys Lys Lys Lys Lys Lys Lys Lys Lys Lys Lys Lys Lys Lys Lys
130                 135                 140

Lys Lys Lys Lys Lys Lys Lys Lys Lys Lys Lys Lys Lys Lys Lys
145                 150                 155                 160

Lys Lys Lys Lys Lys Lys Lys Lys Lys Lys Lys Lys Lys Lys Lys
            165                 170                 175

Lys Lys Lys Lys Lys Lys Lys Lys Lys Lys Lys Lys Lys Lys Lys
        180                 185                 190

Lys Lys Lys Lys Lys Lys Lys Lys Leu Leu Leu Leu Leu Leu Leu
    195                 200                 205

Leu Leu Leu
    210

<210> SEQ ID NO 27
<211> LENGTH: 220
<212> TYPE: PRT
<213> ORGANISM: Artificial Sequence
<220> FEATURE:
<223> OTHER INFORMATION: K200L20

<400> SEQUENCE: 27

Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys
            20                  25                  30

Lys Lys Lys Lys Lys Lys Lys Lys Lys Lys Lys Lys Lys Lys Lys
        35                  40                  45

Lys Lys Lys Lys Lys Lys Lys Lys Lys Lys Lys Lys Lys Lys Lys
    50                  55                  60

Lys Lys Lys Lys Lys Lys Lys Lys Lys Lys Lys Lys Lys Lys Lys
65                  70                  75                  80

Lys Lys Lys Lys Lys Lys Lys Lys Lys Lys Lys Lys Lys Lys Lys
                85                  90                  95

Lys Lys Lys Lys Lys Lys Lys Lys Lys Lys Lys Lys Lys Lys Lys
            100                 105                 110

Lys Lys Lys Lys Lys Lys Lys Lys Lys Lys Lys Lys Lys Lys Lys
        115                 120                 125

Lys Lys Lys Lys Lys Lys Lys Lys Lys Lys Lys Lys Lys Lys Lys
    130                 135                 140

Lys Lys Lys Lys Lys Lys Lys Lys Lys Lys Lys Lys Lys Lys Lys
145                 150                 155                 160

Lys Lys Lys Lys Lys Lys Lys Lys Lys Lys Lys Lys Lys Lys Lys
                165                 170                 175

Lys Lys Lys Lys Lys Lys Lys Lys Lys Lys Lys Lys Lys Lys Lys
            180                 185                 190

Lys Lys Lys Lys Lys Lys Lys Leu Leu Leu Leu Leu Leu Leu
        195                 200                 205

Leu Leu Leu Leu Leu Leu Leu Leu Leu Leu Leu
    210                 215                 220

<210> SEQ ID NO 28
<211> LENGTH: 230
<212> TYPE: PRT
<213> ORGANISM: Artificial Sequence
<220> FEATURE:
<223> OTHER INFORMATION: K200L30

<400> SEQUENCE: 28

Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys
            20                  25                  30

Lys Lys Lys Lys Lys Lys Lys Lys Lys Lys Lys Lys Lys Lys Lys
        35                  40                  45

Lys Lys Lys Lys Lys Lys Lys Lys Lys Lys Lys Lys Lys Lys Lys
    50                  55                  60

Lys Lys Lys Lys Lys Lys Lys Lys Lys Lys Lys Lys Lys Lys Lys
65                  70                  75                  80

Lys Lys Lys Lys Lys Lys Lys Lys Lys Lys Lys Lys Lys Lys Lys
                85                  90                  95

Lys Lys Lys Lys Lys Lys Lys Lys Lys Lys Lys Lys Lys Lys Lys
            100                 105                 110

Lys Lys Lys Lys Lys Lys Lys Lys Lys Lys Lys Lys Lys Lys Lys
        115                 120                 125

Lys Lys Lys Lys Lys Lys Lys Lys Lys Lys Lys Lys Lys Lys Lys

```
            130                 135                 140

Lys Lys Lys Lys Lys Lys Lys Lys Lys Lys Lys Lys Lys Lys Lys Lys
145                 150                 155                 160

Lys Lys Lys Lys Lys Lys Lys Lys Lys Lys Lys Lys Lys Lys Lys Lys
                165                 170                 175

Lys Lys Lys Lys Lys Lys Lys Lys Lys Lys Lys Lys Lys Lys Lys Lys
                180                 185                 190

Lys Lys Lys Lys Lys Lys Lys Lys Leu Leu Leu Leu Leu Leu Leu Leu
            195                 200                 205

Leu Leu Leu Leu Leu Leu Leu Leu Leu Leu Leu Leu Leu Leu Leu Leu
        210                 215                 220

Leu Leu Leu Leu Leu Leu
225                 230

<210> SEQ ID NO 29
<211> LENGTH: 240
<212> TYPE: PRT
<213> ORGANISM: Artificial Sequence
<220> FEATURE:
<223> OTHER INFORMATION: K200L40

<400> SEQUENCE: 29

Lys Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys Lys
                20                  25                  30

Lys Lys Lys Lys Lys Lys Lys Lys Lys Lys Lys Lys Lys Lys Lys Lys
            35                  40                  45

Lys Lys Lys Lys Lys Lys Lys Lys Lys Lys Lys Lys Lys Lys Lys Lys
        50                  55                  60

Lys Lys Lys Lys Lys Lys Lys Lys Lys Lys Lys Lys Lys Lys Lys Lys
65                  70                  75                  80

Lys Lys Lys Lys Lys Lys Lys Lys Lys Lys Lys Lys Lys Lys Lys Lys
                85                  90                  95

Lys Lys Lys Lys Lys Lys Lys Lys Lys Lys Lys Lys Lys Lys Lys Lys
            100                 105                 110

Lys Lys Lys Lys Lys Lys Lys Lys Lys Lys Lys Lys Lys Lys Lys Lys
        115                 120                 125

Lys Lys Lys Lys Lys Lys Lys Lys Lys Lys Lys Lys Lys Lys Lys Lys
130                 135                 140

Lys Lys Lys Lys Lys Lys Lys Lys Lys Lys Lys Lys Lys Lys Lys Lys
145                 150                 155                 160

Lys Lys Lys Lys Lys Lys Lys Lys Lys Lys Lys Lys Lys Lys Lys Lys
                165                 170                 175

Lys Lys Lys Lys Lys Lys Lys Lys Lys Lys Lys Lys Lys Lys Lys Lys
            180                 185                 190

Lys Lys Lys Lys Lys Lys Lys Lys Leu Leu Leu Leu Leu Leu Leu Leu
        195                 200                 205

Leu Leu Leu Leu Leu Leu Leu Leu Leu Leu Leu Leu Leu Leu Leu Leu
    210                 215                 220

Leu Leu Leu Leu Leu Leu Leu Leu Leu Leu Leu Leu Leu Leu Leu Leu
225                 230                 235                 240

<210> SEQ ID NO 30
<211> LENGTH: 250
<212> TYPE: PRT
```

<213> ORGANISM: Artificial Sequence
<220> FEATURE:
<223> OTHER INFORMATION: K200L50

<400> SEQUENCE: 30

```
Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys
            20                  25                  30

Lys Lys Lys Lys Lys Lys Lys Lys Lys Lys Lys Lys Lys Lys Lys
            35                  40                  45

Lys Lys Lys Lys Lys Lys Lys Lys Lys Lys Lys Lys Lys Lys Lys
        50                  55                  60

Lys Lys Lys Lys Lys Lys Lys Lys Lys Lys Lys Lys Lys Lys Lys
65                  70                  75                  80

Lys Lys Lys Lys Lys Lys Lys Lys Lys Lys Lys Lys Lys Lys Lys
                85                  90                  95

Lys Lys Lys Lys Lys Lys Lys Lys Lys Lys Lys Lys Lys Lys Lys
            100                 105                 110

Lys Lys Lys Lys Lys Lys Lys Lys Lys Lys Lys Lys Lys Lys Lys
        115                 120                 125

Lys Lys Lys Lys Lys Lys Lys Lys Lys Lys Lys Lys Lys Lys Lys
    130                 135                 140

Lys Lys Lys Lys Lys Lys Lys Lys Lys Lys Lys Lys Lys Lys Lys
145                 150                 155                 160

Lys Lys Lys Lys Lys Lys Lys Lys Lys Lys Lys Lys Lys Lys Lys
                165                 170                 175

Lys Lys Lys Lys Lys Lys Lys Lys Lys Lys Lys Lys Lys Lys Lys
            180                 185                 190

Lys Lys Lys Lys Lys Lys Lys Lys Leu Leu Leu Leu Leu Leu Leu
        195                 200                 205

Leu Leu Leu Leu Leu Leu Leu Leu Leu Leu Leu Leu Leu Leu Leu
    210                 215                 220

Leu Leu Leu Leu Leu Leu Leu Leu Leu Leu Leu Leu Leu Leu Leu
225                 230                 235                 240

Leu Leu Leu Leu Leu Leu Leu Leu Leu Leu
                245                 250
```

<210> SEQ ID NO 31
<211> LENGTH: 100
<212> TYPE: PRT
<213> ORGANISM: Artificial Sequence
<220> FEATURE:
<223> OTHER INFORMATION: K100

<400> SEQUENCE: 31

```
Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys
            20                  25                  30

Lys Lys Lys Lys Lys Lys Lys Lys Lys Lys Lys Lys Lys Lys Lys
            35                  40                  45

Lys Lys Lys Lys Lys Lys Lys Lys Lys Lys Lys Lys Lys Lys Lys
        50                  55                  60

Lys Lys Lys Lys Lys Lys Lys Lys Lys Lys Lys Lys Lys Lys Lys
65                  70                  75                  80
```

Lys Lys Lys Lys Lys Lys Lys Lys Lys Lys Lys Lys Lys Lys Lys
                85                  90                  95

Lys Lys Lys Lys
        100

<210> SEQ ID NO 32
<211> LENGTH: 200
<212> TYPE: PRT
<213> ORGANISM: Artificial Sequence
<220> FEATURE:
<223> OTHER INFORMATION: K200

<400> SEQUENCE: 32

Lys Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys
            20                  25                  30

Lys Lys Lys Lys Lys Lys Lys Lys Lys Lys Lys Lys Lys Lys Lys
        35                  40                  45

Lys Lys Lys Lys Lys Lys Lys Lys Lys Lys Lys Lys Lys Lys Lys
    50                  55                  60

Lys Lys Lys Lys Lys Lys Lys Lys Lys Lys Lys Lys Lys Lys Lys Lys
65                  70                  75                  80

Lys Lys Lys Lys Lys Lys Lys Lys Lys Lys Lys Lys Lys Lys Lys
            85                  90                  95

Lys Lys Lys Lys Lys Lys Lys Lys Lys Lys Lys Lys Lys Lys Lys
        100                 105                 110

Lys Lys Lys Lys Lys Lys Lys Lys Lys Lys Lys Lys Lys Lys Lys
    115                 120                 125

Lys Lys Lys Lys Lys Lys Lys Lys Lys Lys Lys Lys Lys Lys Lys
130                 135                 140

Lys Lys Lys Lys Lys Lys Lys Lys Lys Lys Lys Lys Lys Lys Lys Lys
145                 150                 155                 160

Lys Lys Lys Lys Lys Lys Lys Lys Lys Lys Lys Lys Lys Lys Lys
            165                 170                 175

Lys Lys Lys Lys Lys Lys Lys Lys Lys Lys Lys Lys Lys Lys Lys
        180                 185                 190

Lys Lys Lys Lys Lys Lys Lys Lys
    195                 200